US008589420B2

(12) United States Patent
Kawakami et al.

(10) Patent No.: US 8,589,420 B2
(45) Date of Patent: Nov. 19, 2013

(54) MEDICAL INFORMATION SYSTEM AND PROGRAM FOR SAME

(75) Inventors: Youichi Kawakami, Osaka (JP); Tetsujiro Okamoto, Osaka (JP); Kosuke Sasai, Kobe (JP)

(73) Assignee: Konica Minolta Medical & Graphic, Inc., Tokyo (JP)

(*) Notice: Subject to any disclaimer, the term of this patent is extended or adjusted under 35 U.S.C. 154(b) by 9 days.

(21) Appl. No.: 13/383,053

(22) PCT Filed: Feb. 17, 2010

(86) PCT No.: PCT/JP2010/052308

§ 371 (c)(1), (2), (4) Date: Jan. 9, 2012

(87) PCT Pub. No.: WO2011/004622

PCT Pub. Date: Jan. 13, 2011

(65) Prior Publication Data

US 2012/0117088 A1 May 10, 2012

(30) Foreign Application Priority Data

Jul. 10, 2009 (JP) ................................ 2009-163681

(51) Int. Cl.
*G06F 17/30* (2006.01)

(52) U.S. Cl.
USPC ............................ 707/749; 707/748; 707/752

(58) Field of Classification Search
USPC .................................................. 707/749, 752
See application file for complete search history.

(56) References Cited

U.S. PATENT DOCUMENTS

| | | | | |
|---|---|---|---|---|
| 6,434,569 | B1 | 8/2002 | Toshimitsu et al. | |
| 2005/0076024 | A1 | 4/2005 | Takatsuka et al. | |
| 2007/0168461 | A1* | 7/2007 | Moore | 709/217 |
| 2007/0218519 | A1* | 9/2007 | Urdea et al. | 435/7.92 |
| 2008/0031503 | A1* | 2/2008 | Kanada et al. | 382/128 |
| 2009/0012842 | A1* | 1/2009 | Srinivasan et al. | 705/10 |
| 2009/0024615 | A1* | 1/2009 | Pedro et al. | 707/5 |

FOREIGN PATENT DOCUMENTS

| | | | |
|---|---|---|---|
| JP | 2005-115514 | A | 4/2005 |
| JP | 2005-182179 | A | 7/2005 |
| JP | 2008-181527 | A | 8/2008 |
| JP | 2008-299518 | A | 12/2008 |

OTHER PUBLICATIONS

International Search Report (and an English translation thereof) dated Mar. 16, 2010 issued in counterpart International Application No. PCT/JP2010/052308.

* cited by examiner

*Primary Examiner* — Shyue Jiunn Hwa

(74) *Attorney, Agent, or Firm* — Holtz, Holtz, Goodman & Chick, PC

(57) ABSTRACT

In a medical information system, with respect to a plurality of kinds of medical databases, a plurality of search items included in a search query inputted by a user are sorted in accordance with search divisions, and thereby divided into a finding report search query and a specimen test query. By using these queries, the corresponding databases are searched independently, and individual search results obtained therefrom are combined to generate a combined search result. The individual search result is assigned with an individual score in accordance with the matching degree with the search item. In combining the individual search results, a relevancy score is assigned. The search results are ranked and combined in descending order of the scores. This requires only one issuance of a search execution order without the need to perform a search operation a plurality of times, in order to obtain a desired search result.

13 Claims, 28 Drawing Sheets

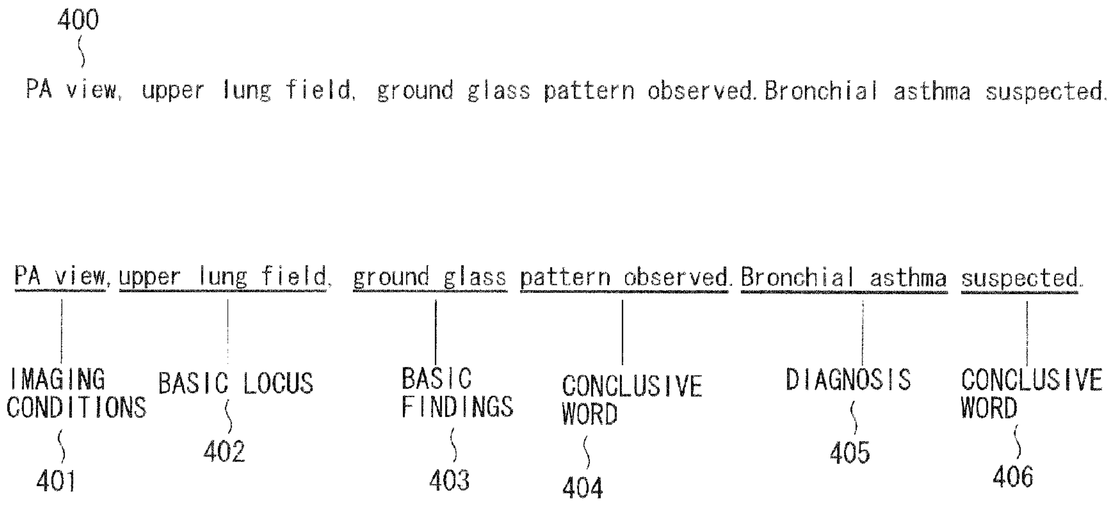
F I G. 4
400
PA view, upper lung field, ground glass pattern observed. Bronchial asthma suspected.
PA view, upper lung field, ground glass pattern observed. Bronchial asthma suspected.
| IMAGING CONDITIONS | BASIC LOCUS | BASIC FINDINGS | CONCLUSIVE WORD | DIAGNOSIS | CONCLUSIVE WORD |
|---|---|---|---|---|---|
| 401 | 402 | 403 | 404 | 405 | 406 |

F I G. 5
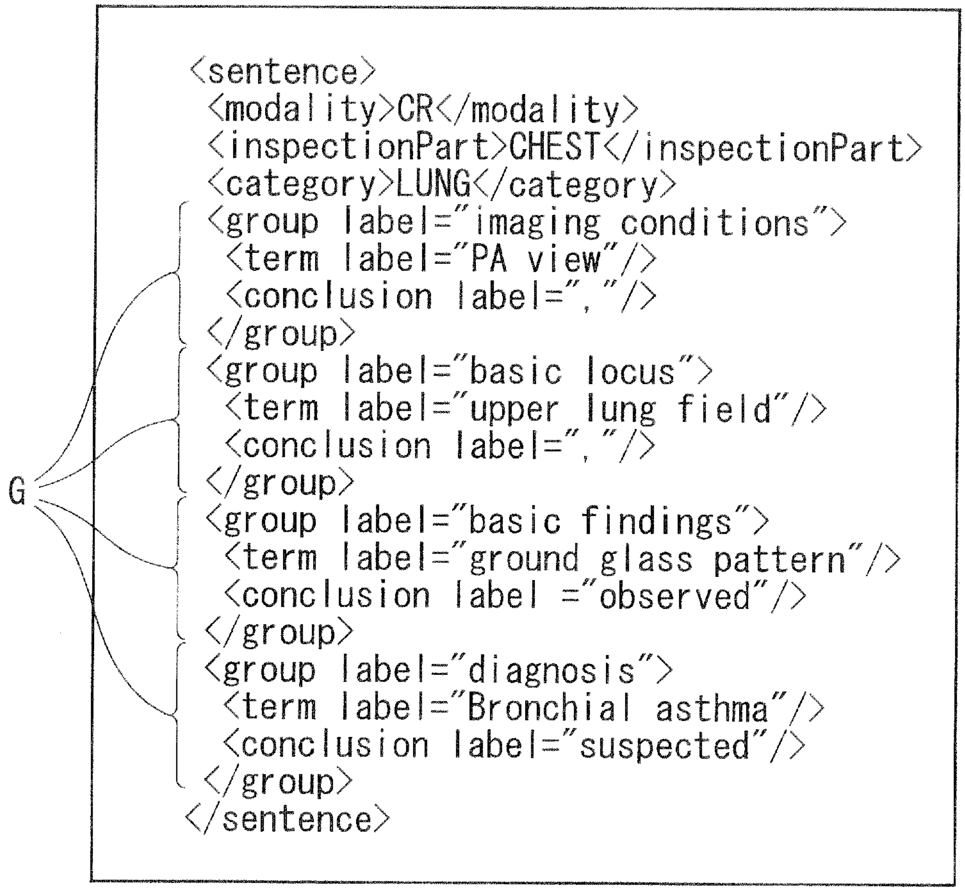

F I G. 6(a)
F I G. 6(b)
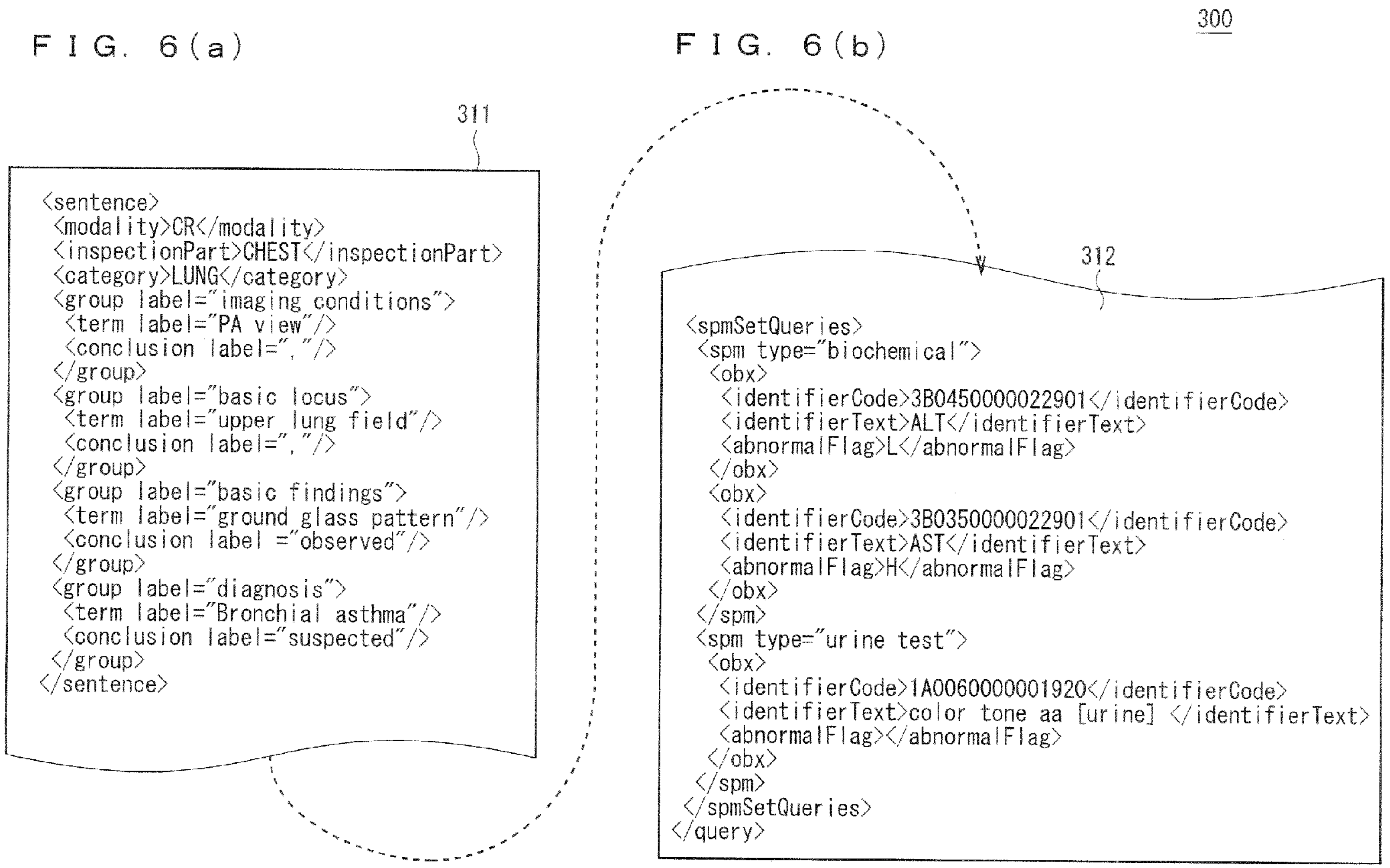

FIG. 9

```
<structured-report>
 <patient lid="1"id="g-0004"name="TARO TANAKA"sex="Male"age="42"/>
 <imageSet>

  <image id="1072"path="c:\temp\0003.jpg"studyId="xxx-0009"
studyDate="2008-07-18T00:00:00"/>
  </imageSet>
  <reportText>PA view, upper lung field and middle lung field, ground glass
pattern observed. Bronchial asthma suspected.</reportText>
  <report>
   <sentence>
    <modality>CR</modality>
    <inspectionPart>CHEST</inspectionPart>
    <category>LUNG</category>
    <reportText>PA view, upper lung field and middle lung field, ground glass
pattern observed. Bronchial asthma suspected.</reportText>
    <group label="imaging conditions">
     <term label="PA view"/>
     <conclusion label=","/>
    </group>
    <group label="basic locus">
     <term label="upper lung field"/>
     <term label="middle lung field"/>
     <conclusion label=","/>
    </group>
    <group label="basic findings">
     <term label="ground glass pattern"/>
     <conclusion label ="observed"/>
    </group>
    <group label="diagnosis">
     <term label="Bronchial asthma"/>
     <conclusion label="suspected"/>
    </group>
  </sentence>
 </report>
</structured-report>
```

FIG. 11

```
 <structured-report>
  <patient lid="4"id="g-0010"name=" HANAKO SUZUKI "
nameKana=" HANAKO SUZUKI "sex="Female"age="56"/>
  <imageSet>
   <image id="5658"path="c:\temp\0123.jpg"studyId="xxx-0100"
studyDate="2008-07-23T00:00:00"/>
  </imageSet>
   <reportText>PA view, upper lung field, stripe observed.
PA view, upper lung field, stripe observed. PA view, middle lung
field, ground glass pattern observed. Bronchial asthma suspected.
</reportText>
  <report>
   <sentence>
    <modality>CR</modality>
    <inspectionPart>CHEST</inspectionPart>
    <category>肺</category>
    <reportText>PA view, upper lung field, stripe observed.
</reportText>
    <group label="imaging conditions">
     <term label="PA view"/>
     <conclusion label=","/>
    </group>
    <group label="basic locus">
     <term label="upper lung field"/>
     <conclusion label=","/>
    </group>
    <group label="basic findings">
     <term label="stripe"/>
     <conclusion label ="observed"/>
    </group>
   </sentence>
```
```
   <sentence>
    <modality>CR</modality>
    <inspectionPart>CHEST</inspectionPart>
    <category>LUNG</category>
    <reportText>PA view, middle lung field, ground glass
pattern observed.
</reportText>
    <group label="imaging conditions">
     <term label="PA view"/>
     <conclusion label=","/>
    </group>
    <group label="basic locus">
     <term label="middle lung field"/>
     <conclusion label=","/>
    </group>
    <group label="basic findings">
     <term label="ground glass pattern"/>
     <conclusion label ="observed"/>
    </group>
   </sentence>
   <sentence>
    <modality>CR</modality>
    <inspectionPart>CHEST</inspectionPart>
    <category>LUNG</category>
    <reportText>Bronchial asthma suspected.</reportText>
    <group label="diagnosis">
     <term label="Bronchial asthma"/>
     <conclusion label="suspected."/>
    </group>
   </sentence>
  </report>
</structured-report>
```

FIG. 12(a)

SEARCH QUERY

| | |
|---|---|
| ITEM A | ABNORMAL VALUE (HIGH) |
| ITEM B | ABNORMAL VALUE (HIGH) |
| ITEM C | NORMAL VALUE |
| ITEM D | ABNORMAL VALUE (LOW) |

FIG. 12(b)

| | |
|---|---|
| ITEM A | ABNORMAL VALUE (HIGH) |
| ITEM B | ABNORMAL VALUE (HIGH) |
| ITEM C | ABNORMAL VALUE (LOW) |
| ITEM D | ABNORMAL VALUE (LOW) |
| ITEM E | NORMAL VALUE |
| ITEM F | ABNORMAL VALUE (HIGH) |

FIG. 12(c)

| | |
|---|---|
| ITEM A | ABNORMAL VALUE (HIGH) |
| ITEM B | ABNORMAL VALUE (HIGH) |
| ITEM C | NORMAL VALUE |
| ITEM D | ABNORMAL VALUE (LOW) |
| ITEM E | NORMAL VALUE |
| ITEM F | NORMAL VALUE |

FIG. 17(a)

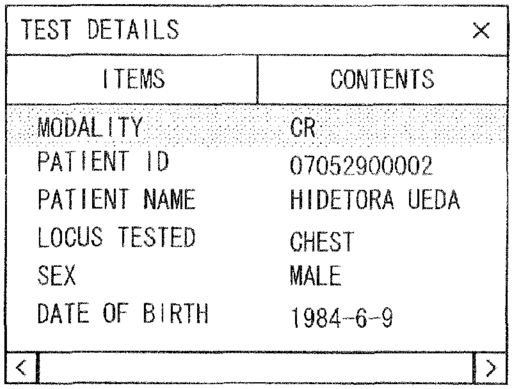

FIG. 17(b)

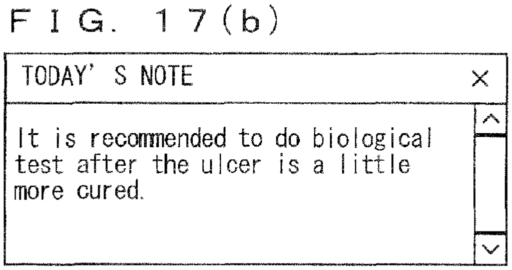

FIG. 17(c)

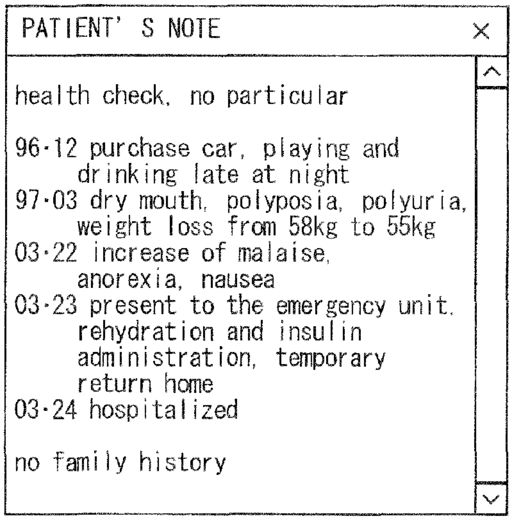

FIG. 17(d)

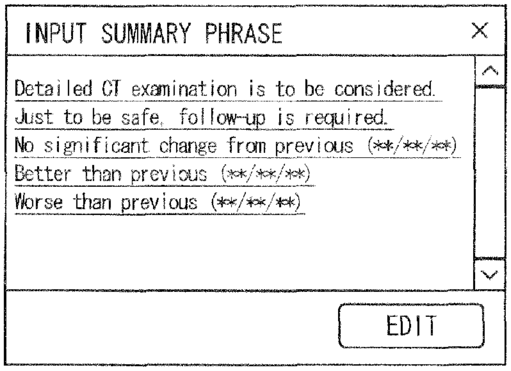

FIG. 17(e)

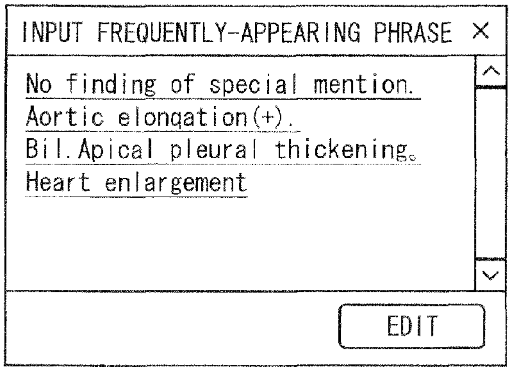

F I G. 1 7 (a)

| TEST DETAILS | | × |
|---|---|---|
| ITEMS | CONTENTS | |
| MODALITY | CR | |
| PATIENT ID | 07052900002 | |
| PATIENT NAME | HIDETORA UEDA | |
| LOCUS TESTED | CHEST | |
| SEX | MALE | |
| DATE OF BIRTH | 1984-6-9 | |

F I G. 1 7 (b)

TODAY'S NOTE　　　　　　×

It is recommended to do biological test after the ulcer is a little more cured.

F I G. 1 7 (c)

PATIENT'S NOTE　　　　　× health check, no particular

96・12 purchase car, playing and
　　　drinking late at night
97・03 dry mouth, polyposia, polyuria,
　　　weight loss from 58kg to 55kg
03・22 increase of malaise,
　　　anorexia, nausea
03・23 present to the emergency unit,
　　　rehydration and insulin
　　　administration, temporary
　　　return home
03・24 hospitalized no family history F I G. 1 7 (d)

INPUT SUMMARY PHRASE　　　　×

Detailed CT examination is to be considered.
Just to be safe, follow-up is required.
No significant change from previous (\*\*/\*\*/\*\*)
Better than previous (\*\*/\*\*/\*\*)
Worse than previous (\*\*/\*\*/\*\*)

[ EDIT ]

F I G. 1 7 (e)

INPUT FREQUENTLY-APPEARING PHRASE　×

No finding of special mention.
Aortic elongation(+).
Bil.Apical pleural thickening.
Heart enlargement

[ EDIT ]

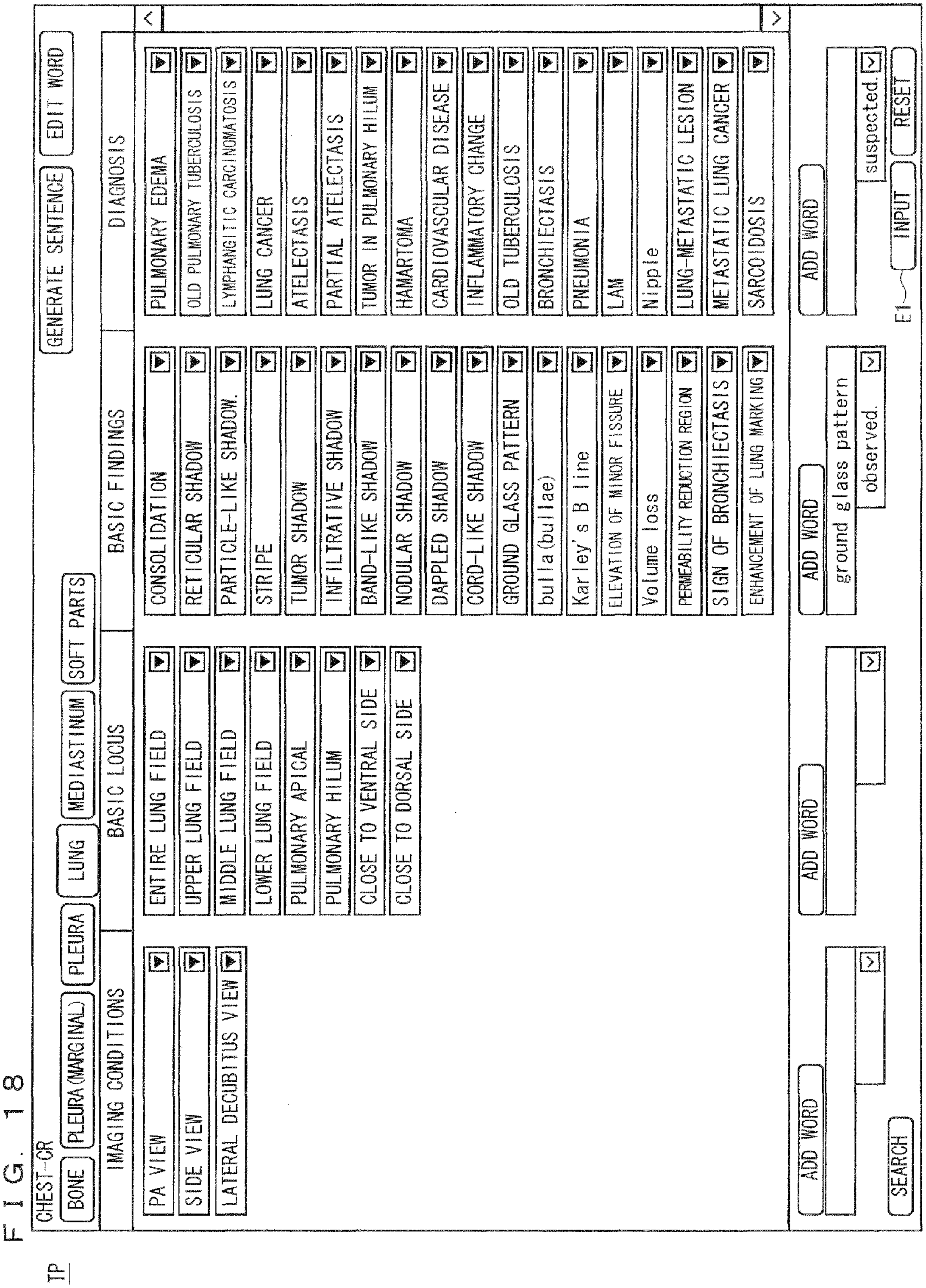

FIG. 18

CHEST-CR
[BONE] [PLEURA(MARGINAL)] [PLEURA] [LUNG] [MEDIASTINUM] [SOFT PARTS]    [GENERATE SENTENCE] [EDIT WORD]

| IMAGING CONDITIONS | BASIC LOCUS | BASIC FINDINGS | DIAGNOSIS |
|---|---|---|---|
| PA VIEW ▼ | ENTIRE LUNG FIELD ▼ | CONSOLIDATION ▼ | PULMONARY EDEMA ▼ |
| SIDE VIEW ▼ | UPPER LUNG FIELD ▼ | RETICULAR SHADOW ▼ | OLD PULMONARY TUBERCULOSIS ▼ |
| LATERAL DECUBITUS VIEW ▼ | MIDDLE LUNG FIELD ▼ | PARTICLE-LIKE SHADOW ▼ | LYMPHANGITIC CARCINOMATOSIS ▼ |
| | LOWER LUNG FIELD ▼ | STRIPE ▼ | LUNG CANCER ▼ |
| | PULMONARY APICAL ▼ | TUMOR SHADOW ▼ | ATELECTASIS ▼ |
| | PULMONARY HILUM ▼ | INFILTRATIVE SHADOW ▼ | PARTIAL ATELECTASIS ▼ |
| | CLOSE TO VENTRAL SIDE ▼ | BAND-LIKE SHADOW ▼ | TUMOR IN PULMONARY HILUM ▼ |
| | CLOSE TO DORSAL SIDE ▼ | NODULAR SHADOW ▼ | HAMARTOMA ▼ |
| | | DAPPLED SHADOW ▼ | CARDIOVASCULAR DISEASE ▼ |
| | | CORD-LIKE SHADOW ▼ | INFLAMMATORY CHANGE ▼ |
| | | GROUND GLASS PATTERN ▼ | OLD TUBERCULOSIS ▼ |
| | | bulla (bullae) ▼ | BRONCHIECTASIS ▼ |
| | | Karley's B line ▼ | PNEUMONIA ▼ |
| | | ELEVATION OF MINOR FISSURE ▼ | LAM ▼ |
| | | Volume loss ▼ | Nipple ▼ |
| | | PERMEABILITY REDUCTION REGION ▼ | LUNG-METASTATIC LESION ▼ |
| | | SIGN OF BRONCHIECTASIS ▼ | METASTATIC LUNG CANCER ▼ |
| | | ENHANCEMENT OF LUNG MARKING ▼ | SARCOIDOSIS ▼ |

[ADD WORD] [    ▼]    [ADD WORD] [    ▼]    [ADD WORD] [ground glass pattern observed ▼]    [ADD WORD] [suspected. ▼]

[SEARCH]    E1—[INPUT] [RESET]

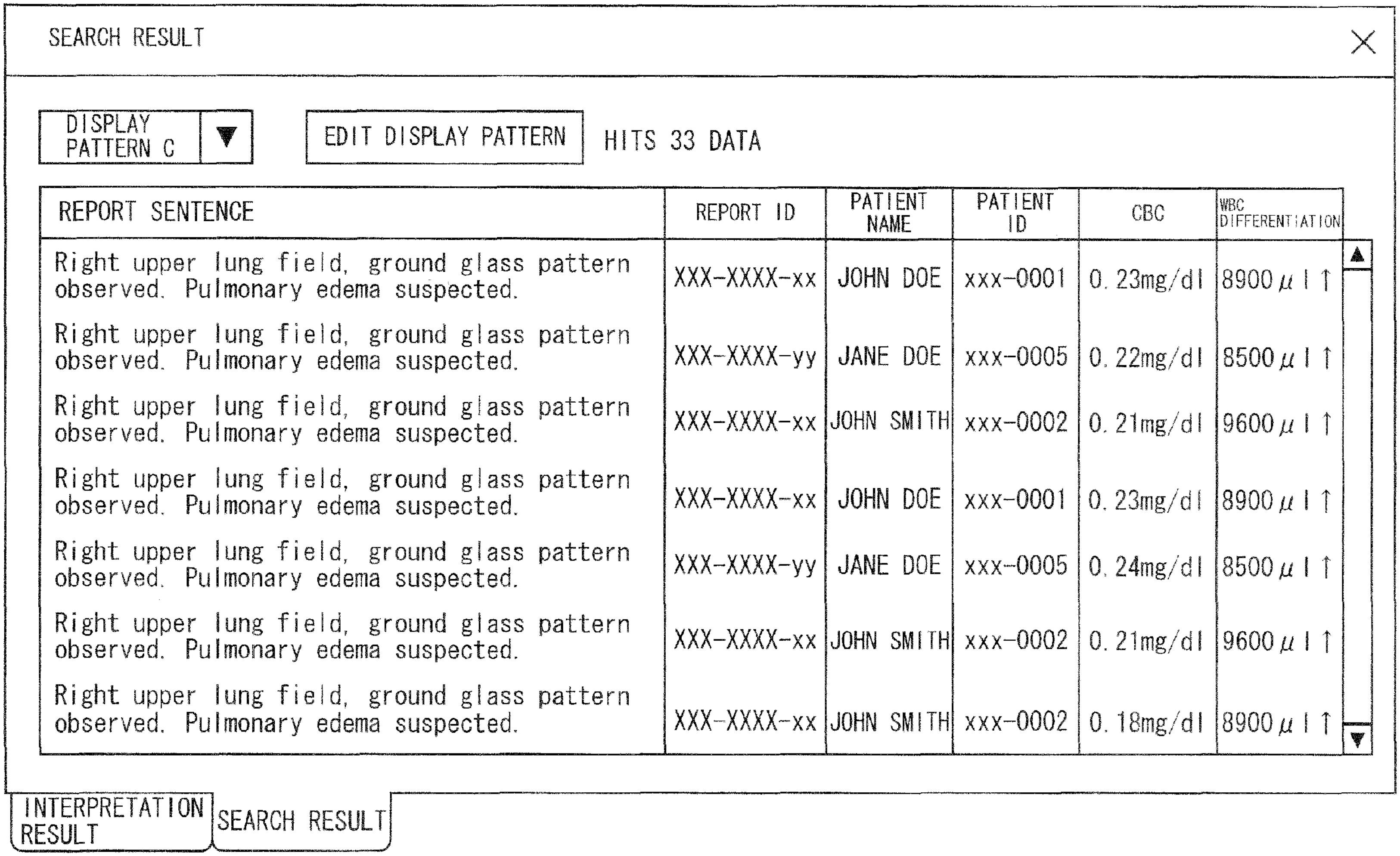

FIG. 22

SEARCH RESULT

DISPLAY PATTERN C ▼ | EDIT DISPLAY PATTERN | HITS 33 DATA

| REPORT SENTENCE | REPORT ID | PATIENT NAME | PATIENT ID | CBC | WBC DIFFERENTIATION |
|---|---|---|---|---|---|
| Right upper lung field, ground glass pattern observed. Pulmonary edema suspected. | XXX-XXXX-xx | JOHN DOE | xxx-0001 | 0.23mg/dl | 8900 μl ↑ |
| Right upper lung field, ground glass pattern observed. Pulmonary edema suspected. | XXX-XXXX-yy | JANE DOE | xxx-0005 | 0.22mg/dl | 8500 μl ↑ |
| Right upper lung field, ground glass pattern observed. Pulmonary edema suspected. | XXX-XXXX-xx | JOHN SMITH | xxx-0002 | 0.21mg/dl | 9600 μl ↑ |
| Right upper lung field, ground glass pattern observed. Pulmonary edema suspected. | XXX-XXXX-xx | JOHN DOE | xxx-0001 | 0.23mg/dl | 8900 μl ↑ |
| Right upper lung field, ground glass pattern observed. Pulmonary edema suspected. | XXX-XXXX-yy | JANE DOE | xxx-0005 | 0.24mg/dl | 8500 μl ↑ |
| Right upper lung field, ground glass pattern observed. Pulmonary edema suspected. | XXX-XXXX-xx | JOHN SMITH | xxx-0002 | 0.21mg/dl | 9600 μl ↑ |
| Right upper lung field, ground glass pattern observed. Pulmonary edema suspected. | XXX-XXXX-xx | JOHN SMITH | xxx-0002 | 0.18mg/dl | 8900 μl ↑ |

INTERPRETATION RESULT | SEARCH RESULT

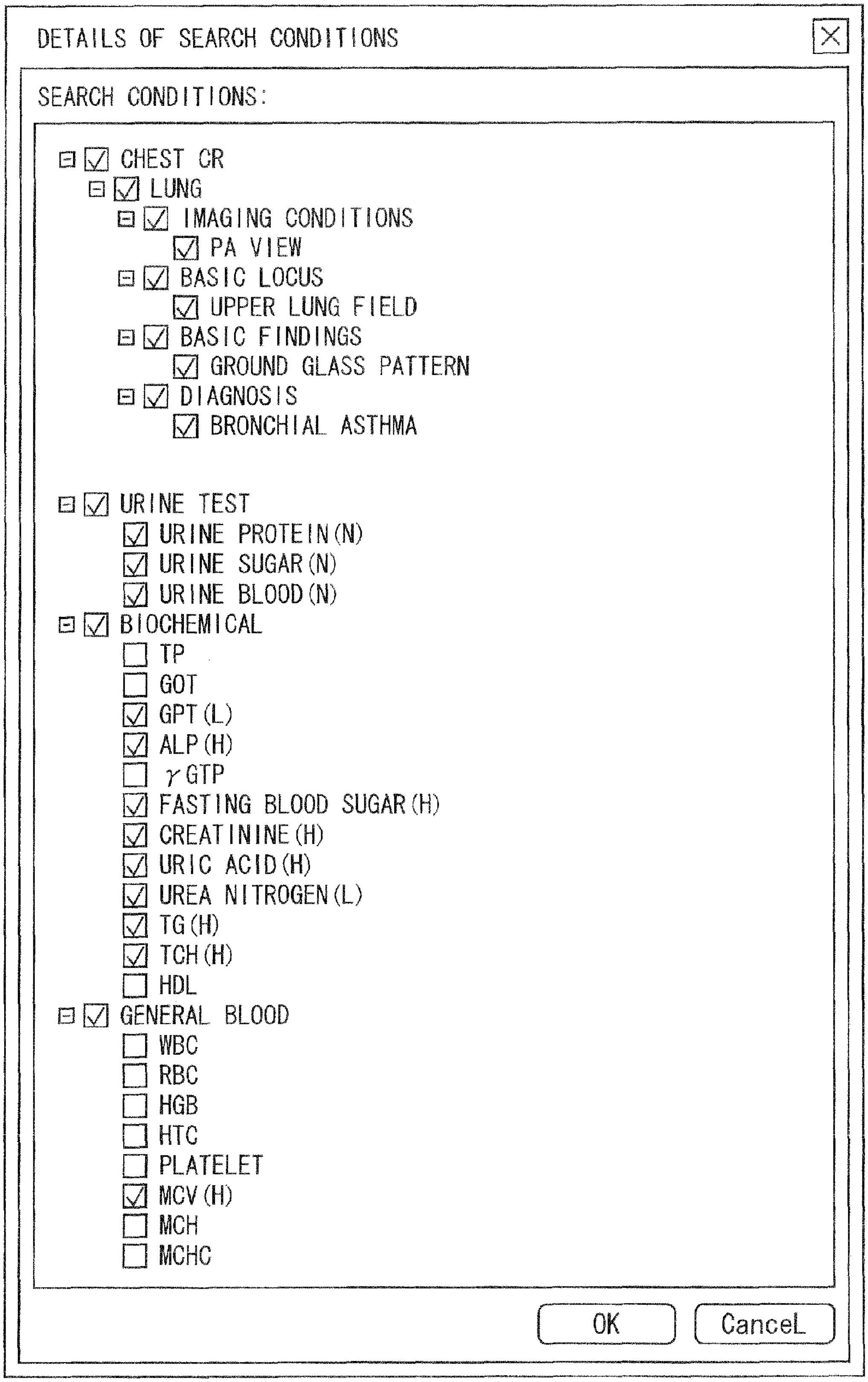

F I G . 2 4

DETAILS OF SEARCH CONDITIONS ☒

SEARCH CONDITIONS:

☑ CHEST CR
   ☑ LUNG
      ☑ IMAGING CONDITIONS
         ☑ PA VIEW
      ☑ BASIC LOCUS
         ☑ UPPER LUNG FIELD
      ☑ BASIC FINDINGS
         ☑ GROUND GLASS PATTERN
      ☑ DIAGNOSIS
         ☑ BRONCHIAL ASTHMA

☑ URINE TEST
   ☑ URINE PROTEIN(N)
   ☑ URINE SUGAR(N)
   ☑ URINE BLOOD(N)
☑ BIOCHEMICAL
   ☐ TP
   ☐ GOT
   ☑ GPT(L)
   ☑ ALP(H)
   ☐ $\gamma$GTP
   ☑ FASTING BLOOD SUGAR(H)
   ☑ CREATININE(H)
   ☑ URIC ACID(H)
   ☑ UREA NITROGEN(L)
   ☑ TG(H)
   ☑ TCH(H)
   ☐ HDL
☑ GENERAL BLOOD
   ☐ WBC
   ☐ RBC
   ☐ HGB
   ☐ HTC
   ☐ PLATELET
   ☑ MCV(H)
   ☐ MCH
   ☐ MCHC

[ OK ]  [ Cancel ]

F I G. 2 5
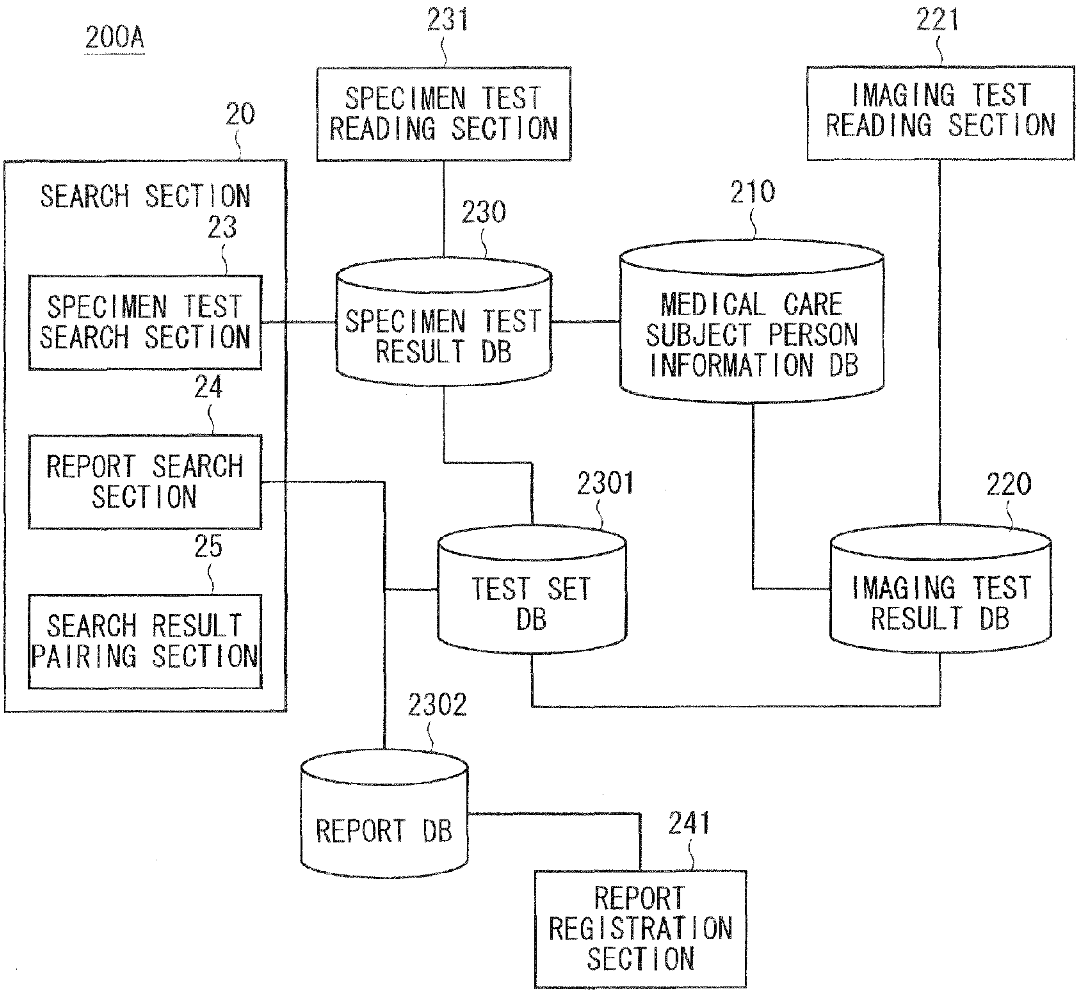

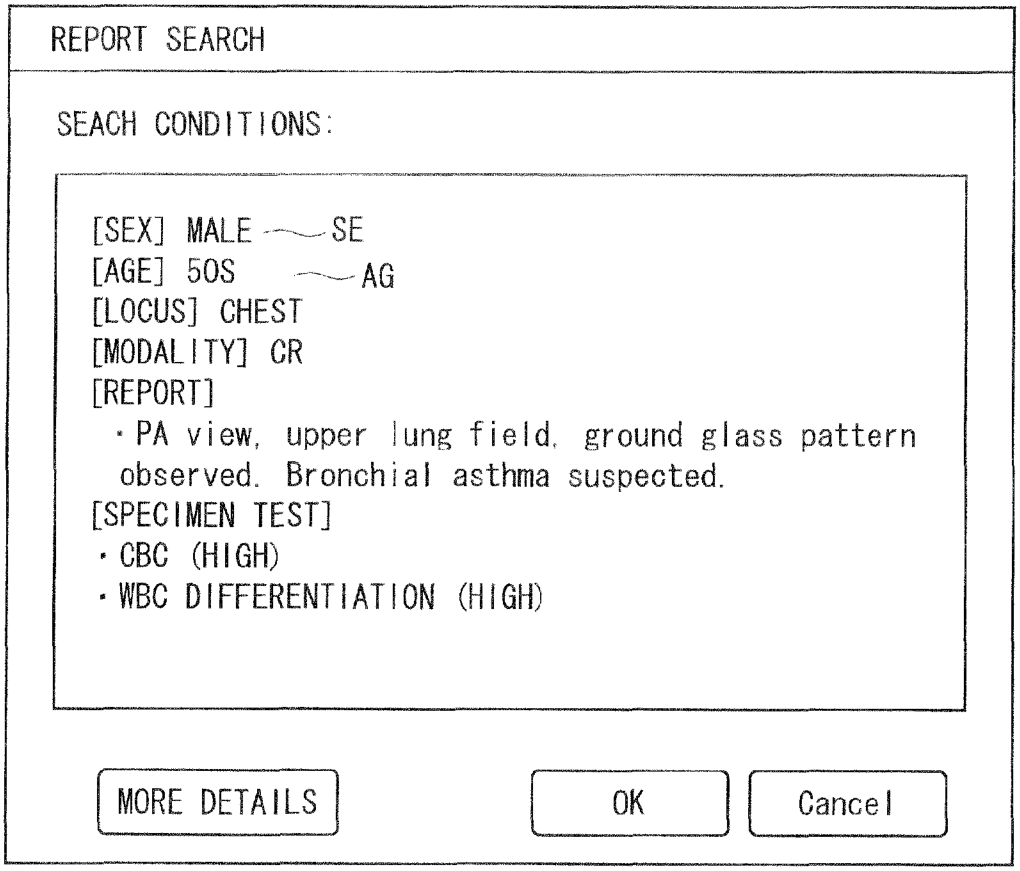
F I G . 2 8
```
REPORT SEARCH

SEACH CONDITIONS:

    [SEX] MALE ──SE
    [AGE] 50S    ──AG
    [LOCUS] CHEST
    [MODALITY] CR
    [REPORT]
      · PA view, upper lung field, ground glass pattern
        observed. Bronchial asthma suspected.
    [SPECIMEN TEST]
     · CBC (HIGH)
     · WBC DIFFERENTIATION (HIGH)

    [MORE DETAILS]            [ OK ]   [ Cancel ]
```

MEDICAL INFORMATION SYSTEM AND PROGRAM FOR SAME

This application is a U.S. National Phase Application under 35 USC 371 of International Application PCT/JP2010/052308 filed Feb. 17, 2010.

TECHNICAL FIELD

The present invention relates to a new technique for a search in a medical information system.

BACKGROUND ART

In recent years, for efficient use of previous information, a search system is widely implemented which searches a database including various data systematically managed and accumulated, and obtains and presents a search result corresponding to a search query (conditions) made up of a keyword and the like.

In a medical field, too, in a diagnosis by a doctor, previous medical information such as a large number of imaging tests, specimen tests, interpretation reports, and the like serves as important reference information, and therefore a technique has been developed in which the medical information is, in the form of electronic data, managed and accumulated in a database system.

On the other hand, the conventional medical database cannot be practically used for accumulating and searching medical images because the medical image has a very large image size. Therefore, if it is necessary to refer to an image together with text data, a designated film is extracted from a film holder to refer to an analog image. Thus, although text information such as medical charts, interpretation reports, and test results can be stored in an electronic form and electronically displayed on a display screen of a CRT or the like, it is impossible that a high-resolution medical image is stored and displayed in an electronic form together with the text information.

To address such a problem, a medical information system has been provided in which information necessary for diagnoses such as medical charts, medical images, interpretation reports, and test results is stored in an electronic form and necessary information can be displayed on a screen by a simple operation, and additionally, test information or the like can be searched and a predetermined image and a test list can be automatically displayed (for example, Japanese Patent Application Laid-Open No. 2008-181527).

SUMMARY OF THE INVENTION

Problems to be Solved by the Invention

However, in a medical information system in which imaging tests, specimen tests, interpretation reports, and the like are distributed among a plurality of databases and independently managed and accumulated, in order to extract information based on a plurality of search conditions, there is no alternative but to separately input a search query to each independent database and combine information extracted from the respective databases based on user's (doctor's) experience. Thus, an enormous amount of time and effort is required for displaying a similar case.

This problem occurs not only in searching for data for a medical care of a particular patient such as a test result, but also generally in searching a database of a wider range of medicine data ("medical data"), including medical literature such as a case report and pharmacological information of medicine.

This is associated with a situation where it is difficult to accumulate all information in a single database because of a tendency that an enormous amount of data is accumulated in the medical field and additionally because healthcare professionals deal with different databases due to separation of medical care departments, specialization of medicine tests, and the like.

The present invention is made in view of the circumstances described above, and an object of the present invention is to provide a technique capable of, in a plurality of databases in which a plurality of kinds of medical data information are accumulated, efficiently obtaining a desired search result by issuing a single search execution order without any complication that requires a user to combine, based on his/her experience, information obtained as a result of separately searching the plurality of databases with respect to each of the kinds.

Means for Solving the Problems

To achieve the foregoing object, the present invention provides the following means.

A medical information system according to a first aspect is a medical information system including a plurality of databases in which a plurality of kinds of medical data are respectively accumulated, the medical information system including: an input section for inputting a query that includes a plurality of search items; a sorting section for sorting the plurality of search items into a plurality of search divisions corresponding to the plurality of databases, respectively, in accordance with a predetermined sorting rule; a search section for independently searching the plurality of databases by using the search item included in the corresponding search division; and a generation section for combining individual search results extracted respectively from the plurality of databases by the search section, to thereby generate a combined search result.

A medical information system according to a second aspect is the medical information system according to the first aspect, wherein in the plurality of databases, a plurality of kinds of test diagnosis information are accumulated as the medical data in the databases different from one another, the plurality of kinds of test diagnosis information being records of results of different kinds of clinical tests or diagnostic evaluations on the test results.

A medical information system according to a third aspect is the medical information system according to the second aspect, wherein: each of the test diagnosis information includes identification information of a medical care subject person or a medical care subject animal serving as a medical care subject individual; and the generation section generates the combined search result by combining, among the test diagnosis information accumulated in the plurality of databases, the information concerning the same medical care subject individual that is identified based on the identification information.

A medical information system according to a fourth aspect is the medical information system according to the first aspect wherein: the generation section includes an individual score assigning section for assigning an individual score to a content of a data item included in the individual search result obtained from each of the databases in such a manner that a higher score is assigned as the degree of matching with the search item is higher; and the generation section combines, across the databases, the data items of which the individual scores are relatively high in each of the databases, to thereby generate the combined search result.

A medical information system according to a fifth aspect is the medical information system according to the fourth aspect, wherein the individual score is determined based on the ratio of medical data items matching the search items to the medical data in the corresponding database.

A medical information system according to a sixth aspect is the medical information system according to the first aspect wherein: the generation section includes a relevancy score assigning section for assigning, as a relevancy score, a relevancy of the plurality of kinds of individual search results; and the generation section combines, across the databases, the medical data of which the relevancy scores are relatively high, to thereby generate the combined search result.

A medical information system according to a seventh aspect is a medical information system according to the second aspect, wherein: the plurality of kinds of test diagnosis information have attached thereto information of test identification dates of the corresponding clinical tests; the generation section includes a test identification date score assigning section for assigning a relevancy score indicating a relevancy of different kinds of the test diagnosis information, in such a manner that a higher score is assigned as a difference in the test identification date is smaller; and the generation section combines, across the databases, the test diagnosis information of which the relevancy scores are relatively high, to thereby generate the combined search result.

A medical information system according to an eighth aspect is the medical information system according to the first aspect, wherein the plurality of databases include a database of at least one of test diagnosis information, nursing care data, electronic medical chart information, and patient information.

A medical information system according to a ninth aspect is the medical information system according to the eighth aspect, wherein the plurality of databases include a specimen test result database in which a result of a specimen test is accumulated as the test diagnosis information.

A medical information system according to a tenth aspect is the medical information system according to the eighth aspect, wherein: the plurality of databases include an imaging test result database in which a test image is accumulated, and a finding report storing database in which a finding report corresponding to each test image is accumulated; the search section searches the finding report storing database, for the search item sorted into the search division of an imaging test; and the generation section includes a test image extraction section for, based on test-image-specific information attached to the finding report obtained as the individual search result, extracting the test image corresponding to the finding report from the imaging test result database, and incorporating the test image into the combined search result.

A medical information system according to an eleventh aspect is the medical information system according to the tenth aspect, wherein: the generation section includes a report matching degree identification section for identifying the matching degree of each finding report based on how any sentences in the finding report a content matching the search item appears; and the generation section sets an individual score of each finding report in searching the finding report storing database, based on the matching degree.

A medical information system according to a twelfth aspect is the medical information system according to the eleventh aspect, wherein the finding report includes a structured-document.

A medical information system according to a thirteenth aspect is the medical information system according to the twelfth aspect, wherein the search for the finding report is the structured-document search.

A medical information system according to a fourteenth aspect is the medical information system according to the twelfth aspect, wherein the structured document is described in RDF.

A medical information system according to a fifteenth aspect is the medical information system according to the first aspect, wherein: a plurality of kinds of medical data based on which a predetermined diagnosis has been previously done are stored across at least two of the plurality of databases; the medical information system further includes a set information database storing information that identifies a set of the plurality of kinds of medical data; and the generation section refers to the set information database, when combining the plurality of individual search results to obtain the combined search result.

A medical information system according to a sixteenth aspect is a program installed in a computer system including a plurality of databases in which different kinds of medical data are accumulated, the program being executed to cause the computer system to function as a medical information system including: an input section for inputting a query that includes a plurality of search items; a sorting section for sorting the plurality of search items into a plurality of search divisions corresponding to the plurality of databases, respectively, in accordance with a predetermined sorting rule; a search section for independently searching the plurality of databases by using the search item included in the corresponding search division; and a generation section for combining individual search results extracted respectively from the plurality of databases by the search section, to thereby generate a combined search result.

Effects of the Invention

In the medical information system according to the first to sixteenth aspects, in the medical information system including the plurality of databases, a desired search result can be obtained by only one search execution order in response to a search request including the plurality of search divisions. Therefore, the desired search result can be obtained efficiently.

In the medical information system according to the third aspect, search results concerning the same medical care subject individual are combined, and thereby a plurality of kinds of test diagnosis information concerning the same medical care subject individual can be combined. Thus, a medical determine can be made more appropriately.

In the medical information system according to the fourth aspect, the score is individually assigned to each of the individual search results obtained as a result of independent searches. Thus, a pre-processing can be performed for efficiently calculating the final search score.

In the medical information system according to the sixth aspect, the relevancy score is assigned to a linkage of object data items in each database, which can serve as an indicator to the user indicating which combination of search results is closest to the desired one.

In the medical information system according to the seventh aspect, in associating the plurality of kinds of test diagnosis information, the test identification date of each test diagnosis information is utilized, and thereby a combined search result having a high relevancy can be obtained.

In the medical information system according to the eighth aspect, a specimen test such as a blood test and a urine test is incorporated into the search result, and thereby a proper search result can be presented in accordance with a situation desired by the user.

In the medical information system according to the tenth aspect, for the search for the test image in response to the query, the finding report is searched for, and thereby the corresponding test image can be indirectly identified and extracted. Thus, a proper search result can be presented in accordance with a situation desired by the user.

In the medical information system according to the eleventh aspect, in the individual search result of the finding report, the matching degree is calculated based on how many sentences the content matching the search item appears. Thus, a pre-processing can be performed for efficiently calculating the final search score.

In the medical information system according to the twelfth aspect, the finding report includes the structured document. Thereby, the database can be configured to store information associating a plurality of items with each other.

In the medical information system according to the thirteenth aspect, the search for the finding report is the structured-document search. This enables the search to be performed with a higher accuracy than a full text search. Thus, a proper search result can be presented in accordance with a situation desired by the user.

In the medical information system according to the fourteenth aspect, the finding report is structured by using the RDF. Thereby, information associating a plurality of items to each other can be easily and properly generated.

In the medical information system according to the fifteenth aspect, by referring to the set information database, a plurality of kinds of medical data closely related to each other can be easily identified.

BRIEF DESCRIPTION OF THE DRAWINGS

FIG. 4 An explanatory diagram showing an example of a sentence structure.

FIG. 5 A diagram showing an example of an inner structure of a sentence corresponding to FIG. 4.

FIG. 6 A diagram showing an example of a query including both a finding report and a specimen test.

FIG. 9 A diagram showing an example of structuration of the finding report of FIG. 8.

FIG. 11 A diagram showing an example of structuration of the finding report of FIG. 10.

FIG. 12 A diagram explaining an algorithm of a specimen test search.

FIG. 17 A diagram for explaining a display of detailed items of the screen of the report system.

FIG. 18 A diagram showing a display example of an input-support template display.

FIG. 22 A diagram showing an example of a display of a search result.

FIG. 24 A diagram showing an example of a display of a dialog box for modifying a search query.

FIG. 25 A block diagram showing a configuration of a server according to a second embodiment.

FIG. 28 A diagram showing a dialog box for confirmation of a search query according to a third embodiment.

EMBODIMENT FOR CARRYING OUT THE INVENTION

1. First Embodiment

1-1. Outline of Medical Information System

Figure 1:
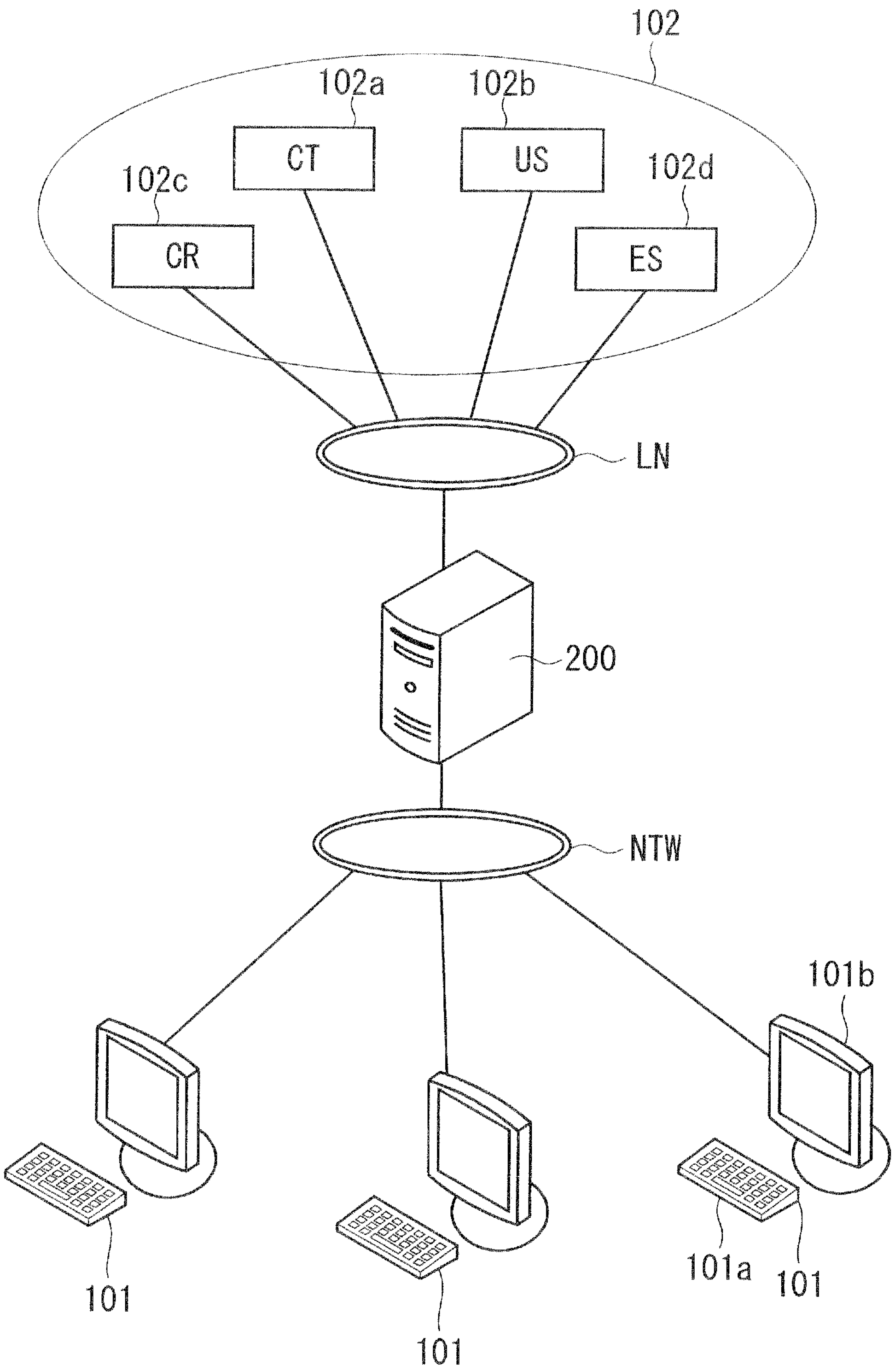
FIG. 1 A diagram showing an example of an outline configuration of a medical information system according to an embodiment of the present invention.

FIG. 1 is a diagram showing an example of an outline configuration of a medical information system 1 according to a first embodiment of the present invention. In FIG. 1, the medical information system 1 is a system for accumulating and managing medical care information in a hospital for performing data processing such as searching and sorting. A medical information server 200 and a plurality of client terminals 101 are connected to a network line NTW such as LAN, in a manner allowing mutual data transmission and reception. Each of the client terminals 101 is configured using a personal computer, and executes client software to thereby implement various computation functions and storage functions which will be described later. Each of the client terminals 101 includes an operation input section 101*a* such as a keyboard, and a display 101*b*.

A plurality of modality (medical equipment) terminals 102 are connected to the medical information server 200 via a network line LN in a manner allowing data transmission and reception. The modality terminals 102 include, for example, a computed tomography apparatus (CT) 102*a*, an ultrasonic diagnosis apparatus (US) 102*b*, a general radiographic X-ray testing apparatus (CR) 102*c*, an endoscopic testing apparatus (ES) 102*d*, and the like.

A plurality of kinds of test diagnosis information such as an imaging test, a specimen test, and medical care information are stored as medical data and accumulated in different databases of the medical information server 200. A user (healthcare professional such as a doctor or a nurse) can access the test diagnosis information accumulated in the medical information server 200 through the client terminal 101.

In the present invention, the term "test diagnosis information" is used as a term that represents a concept including both results of different kinds of clinical tests and results of diagnostic evaluation on the test results. That is, the term is used to represent a concept including not only numerical values, tables, graphs, images, sounds, and moving images, but also documents such as sentences and meta-documents.

The term "specimen" means an object-to-be-tested that is excreted or obtained from a test subject (in this embodiment, a human body), and the term "specimen test" includes a microbiological test, a serological test, a hematological test, a biochemical test, a pathological test, and the like.

On the medical information server 200, server software is running, and the information can be handled. From the client software running on the client terminal 101, the user can access the test diagnosis information within the server 200 through the server software.

As long as the modality terminal 102 is connected online to the medical information server 200, information such as an image obtained by the modality can be transferred online to the medical information server 200 and accumulated in a database within the server 200. Some tests including the specimen test outsourced to an external organization are not online, and therefore the user inputs received test diagnosis information through the operation input section 101*a* of the client terminal 101, to accumulate the received test diagnosis information in a database within the server 200.

<1-1-1. Configuration of Medical Information Server>

Figure 2:
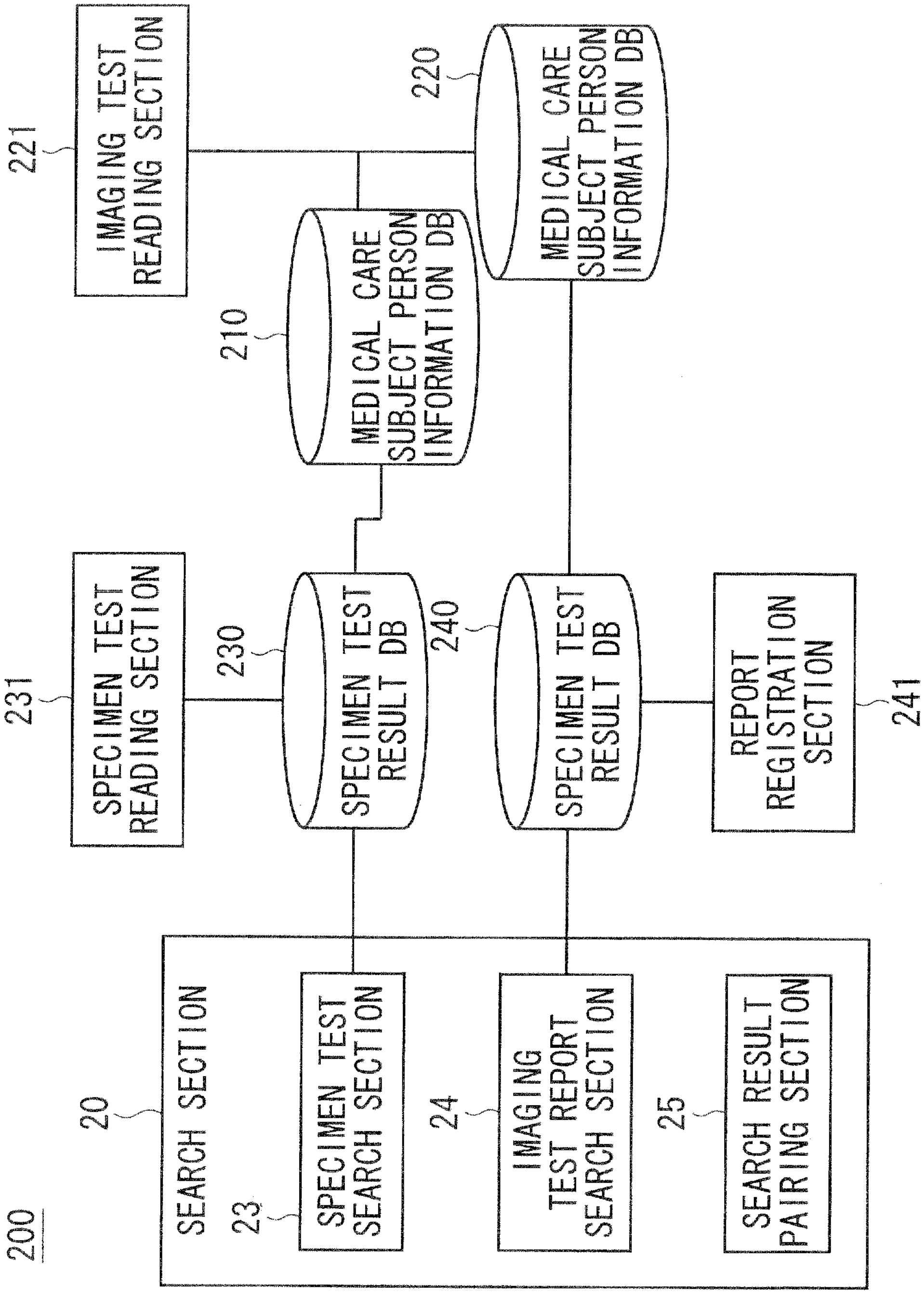
FIG. 2 A block diagram showing a functional configuration of a server of the medical information system.

FIG. 2 is a block diagram showing a basic functional configuration of the medical information server 200. With reference to FIG. 2, a specific description will be given to the test diagnosis information (medical care subject person information, an imaging test result, a specimen test result, and an imaging test report) stored in the medical information server 200.

Medical Care Subject Person Information:

Information concerning the medical care subject person, such as an attribution (a medical care subject person ID, the name, the birth date, the age, the sex, and the like) and a visit history of the medical care subject person, is stored in a medical care subject person information database (DB) 210. That is the medical care subject person information DB 210 includes a list of a large number of medical care subject persons.

Imaging Test Result:

Image data obtained by the modality, to which information concerning an attribution (DICOM attribution) of a DICOM (Digital Image and Communications in Medicine) is given, is stored in an imaging test result DB 220. Here, irrespective of online or offline, the imaging test result is accumulated through an imaging test reading section 221. For identifying the image data, the imaging test result has attached thereto information (basic identification information) indicating a medical care subject person ID, a test ID, a test date, a test object locus, a modality indicating imaging conditions, the number of images, and the like. Thereby, the imaging test result DB 220 is associated with the medical care subject person information DB 210.

Specimen Test Result:

Information concerning each specimen test result such as a blood test result and a urine test result is stored in a specimen test result DB 230. Here, the specimen test result is accumulated through a specimen test reading section 231 irrespective of online or offline. For identifying specimen test data, the specimen test result has attached thereto the basic identification information indicating the medical care subject person ID, the test ID, the test date, and the like. Thereby, each data stored in the specimen test result DB 230 is associated with personal identification information such as the name, the sex, the age, a past medical history, and the like, of a medical care subject person (normally, a patient) in the medical care subject person information DB 210.

Imaging Test Report:

The imaging test report is a finding report in which a medical finding made by a doctor or a laboratory technician based on the imaging test result is recorded in the form of sentences. The imaging test report is stored in an imaging test report DB 240. In general, the imaging test report belongs to the test diagnosis information in which a diagnostic evaluation on the test result is recorded. In this embodiment, the imaging test report is generated in the client terminal 101, and transferred to the medical information server 200, and stored in the imaging test report DB 240 through a report registration section 241. In the generation of a report of the imaging test result, a natural sentence is not used, but a structured document having a meaning marked up is used. Similarly to the imaging test result, the imaging test report has attached thereto the basic identification information, in order to link the imaging test report data and the imaging test result data to each other for each imaging test. Thereby, the imaging test report DB 240 is associated with not only the imaging test result DB 220 but also the medical care subject person information DB 210.

As shown in FIG. 2, a search section 20 is provided in the medical information server 200. The search section 20 is made up of three sections of a specimen test search section 23, an imaging test report search section 24, and a search result pairing section 25, which are functional divisions implemented by software.

1-2. Algorithm Search Process

Figure 3:
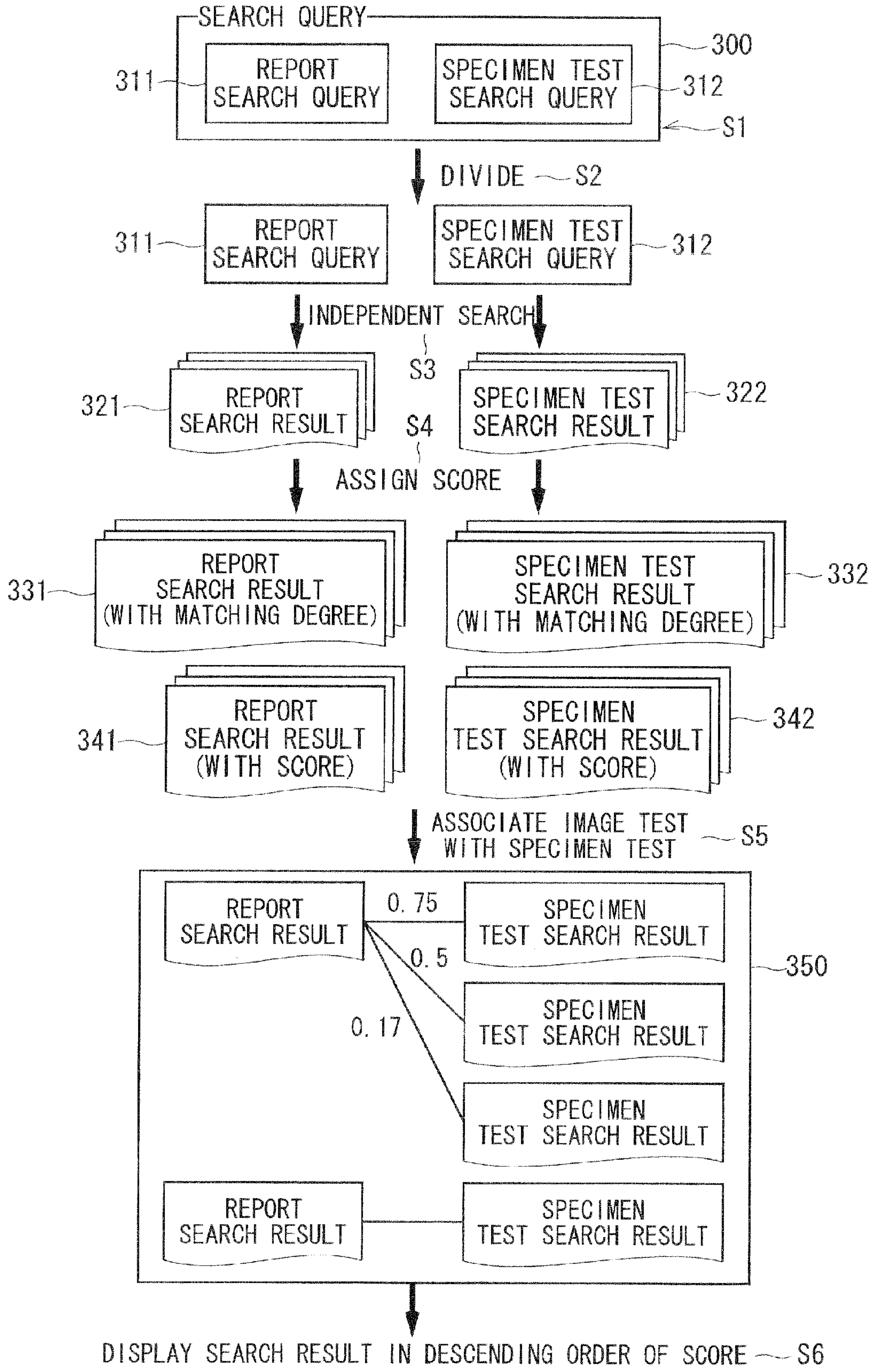
FIG. 3 A diagram for explaining an operation flow of a search process.

FIG. 3 is a flowchart of a search process in the medical information system 1. Hereinafter, operations and an algorithm of the search process will be described along the flowchart of FIG. 3. Any of the operations other than an input operation made by the user are implemented by the cooperation of the client software and the server software mentioned above.

<1-2-1. Division of Search Query>

In step S1 of FIG. 3, the user (typically, the doctor) inputs a search query 300 through the operation input section 101*a* of the client terminal 101. The search query 300 includes a report search query 311 and a specimen test search query 312. In an extremely simplified example, a case "upper lung field and middle lung field, ground glass pattern observed, with abnormally high CRP value" is assumed as the search query 300. In this case, the part "upper lung field and middle lung field, ground glass pattern observed" corresponds to the report search query 311, and the part "with abnormally high CRP value" corresponds to the specimen test search query 312. The user need not start up separate search software to input these two kinds of queries 311 and 312, but the user can input the contents of the search query 300 by single search software on the client terminal 101.

Subsequent operations are based on the functions implemented by the cooperation of the client software and the server software.

Firstly, in step S2, the search query 300 is divided into the finding report search query 311 and the specimen test search query 312. In the aforesaid example, the search query 300 is divided into the finding report search query 311 representing "upper lung field and middle lung field, ground glass pattern observed" and the specimen test search query 312 representing "with abnormally high CRP value".

Here, the expression that the search query 300 is "divided" is a conceptual expression. In a typical aspect of "dividing the query" herein, various search items included in the search query 300 (parent query) are sorted in accordance with a plurality of databases, to thereby generate a plurality of "sub-queries" (here, the finding report search query 311 and the specimen test search query 312).

In general, this corresponds to a process of sorting a plurality of search items included in a search query into a plurality of search divisions corresponding to a plurality databases, respectively, according to predetermined sorting rules. In this embodiment, the query is given as a structured-document so that the sorting rules are expressed by the kind of a tag within the sentence, and the plurality of search divisions are made up of a division regarding the finding report and a division regarding the specimen test.

Then, the two kinds of searches are independently performed (step S3). More specifically, the imaging test report search section 24 searches the imaging test report DB 240 for a report that matches the report search query 311, and extracts corresponding imaging test result data from the imaging test result DB 220. On the other hand, independently of it, the specimen test search section 23 searches the specimen test result DB 230 for test result data that matches the specimen test search query 312. Here, the expression "independent search" means not only that the queries 311 and 312 are separately handled and but also that databases to be searched are different from each other. Each data obtained by the search in this stage is an "individual search result", and specifically, the search is performed based on an algorithm described below.

<1-2-2. Algorithm of Imaging Test Report Search>

Next, an algorithm of the search of the imaging test report (hereinafter also referred to simply as "report") will be described. In a case of a report of a natural sentence, the method of the full text search can be used. However, for a more accurate search, in this embodiment, the report is accumulated in the form of the structured document in the imaging test report DB 240 (FIG. 2). Accordingly, the query for the search is also generated in the form of the structured document.

FIG. 4 is a diagram showing an example of structuration of a sentence portion included in the report or the query. As shown in FIG. 4, a sentence 400 is made up of some groups. FIG. 4 shows an example of structuration of the report or the query concerning the image obtained by performing a general radiographic X-ray test (CR) on a chest. Herein, the sentence 400 is made up of "imaging conditions 401", "basic locus 402", "basic findings 403", "diagnosis 405", and "conclusive word 404" for each of the basic findings 403 and the diagnosis 405. Which groups are included in the sentence depends on a modality, a test locus, and a category.

FIG. 5 shows an example of an inner structure of the sentence portion of FIG. 4. As shown in FIG. 5, the plurality of items included in the sentence are sorted into groups G such as the imaging conditions, the basic locus, the basic finding, and the diagnosis, and are structured.

FIG. 6 shows an example of structuration of the query 300. The query 300 is divided into the finding report search query 311 (FIG. 6A) and the specimen test search query 312 (FIG. 6B). The finding report search query 311 of FIG. 6A is used for the search of the image diagnosis report. The specimen test search query 312 is used for the search of a specimen test which will be described later.

Figure 8:
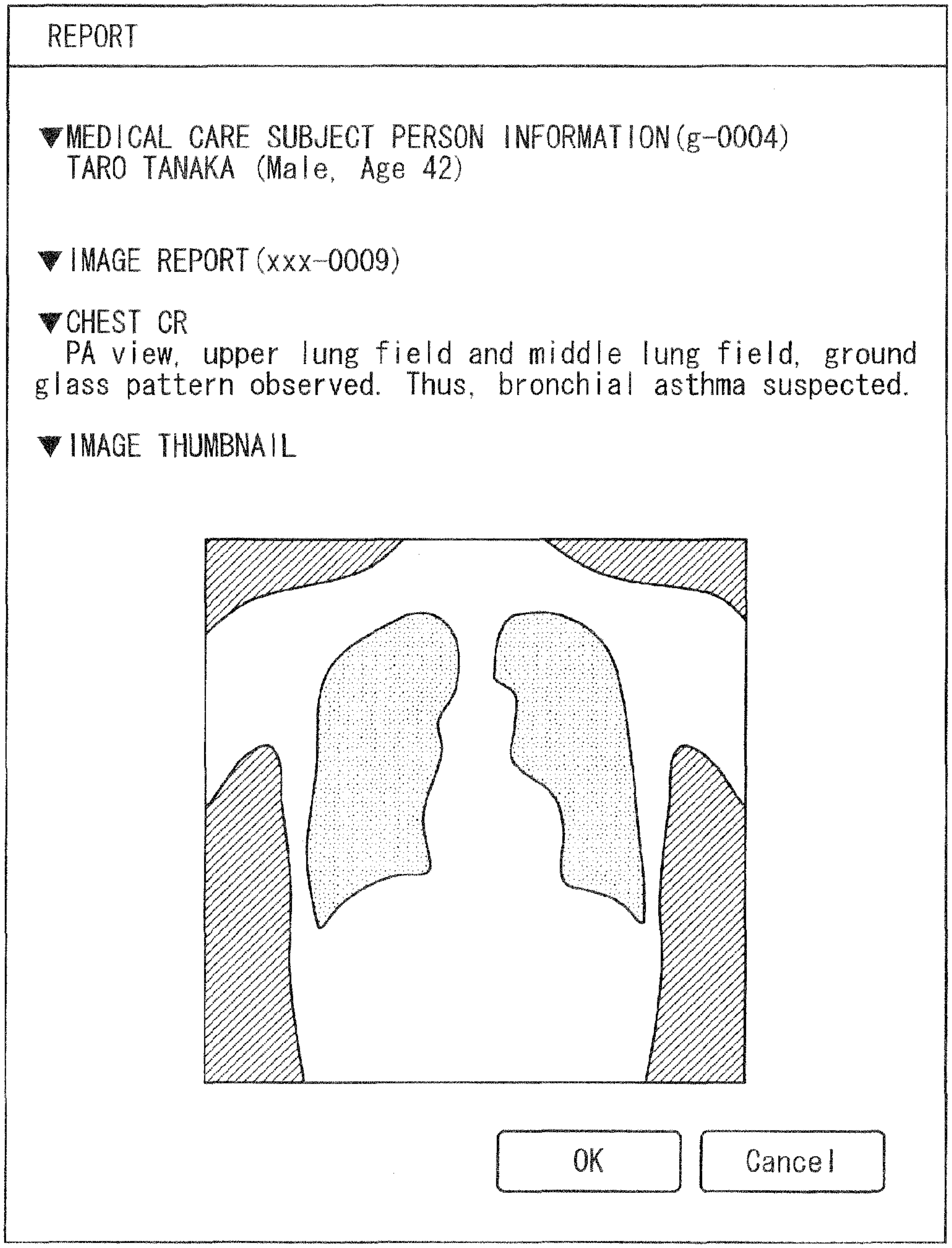
FIG. 8 A diagram showing an example of a finding report existing in an imaging test report DB.

FIG. 9 is a diagram showing an example of an XML expression (inner structure) of the structured document generated and stored as the finding report of FIG. 8. As shown in FIG. 9, a head portion of the sentence indicates that the modality (modality) is the general radiographic X-ray test (CR), that the test locus (inspection part) is a chest (CHEST), and the category (category) is "LUNG". A "group" tag indicates the above-mentioned group. FIG. 11 shows an example of structuration of another report shown in FIG. 10. The example shown in FIG. 11 is different from the example shown in FIG. 9, in that an interpretation result for the upper lung field and an interpretation result for the middle lung field are described in a plurality of separate sentences (sentences).

The report (structured report) in which the sentence is structured as shown in FIG. 9 is accumulated as digital data in the imaging test report DB 240. The search of the finding report concerning the imaging test is a structured-document search performed on the structured-document. Since the sentence is structured, a search of, for example, "a report including 'upper lung field' as the 'basic locus'" is possible. Therefore, a more accurate search than the full text search can be performed.

In may cases, a plurality of finding reports that fully or partially match the finding report search query 311 are found in the imaging test report DB 240. Therefore, by defining the degree of matching (matching degree) with the query 311, it is possible to assist the user to refine the search. The matching degree may be defined variously. In this embodiment, an indicator indicating "whether or not the item that matches the search query appears in several sentences" is defined as the matching degree.

Figure 7:
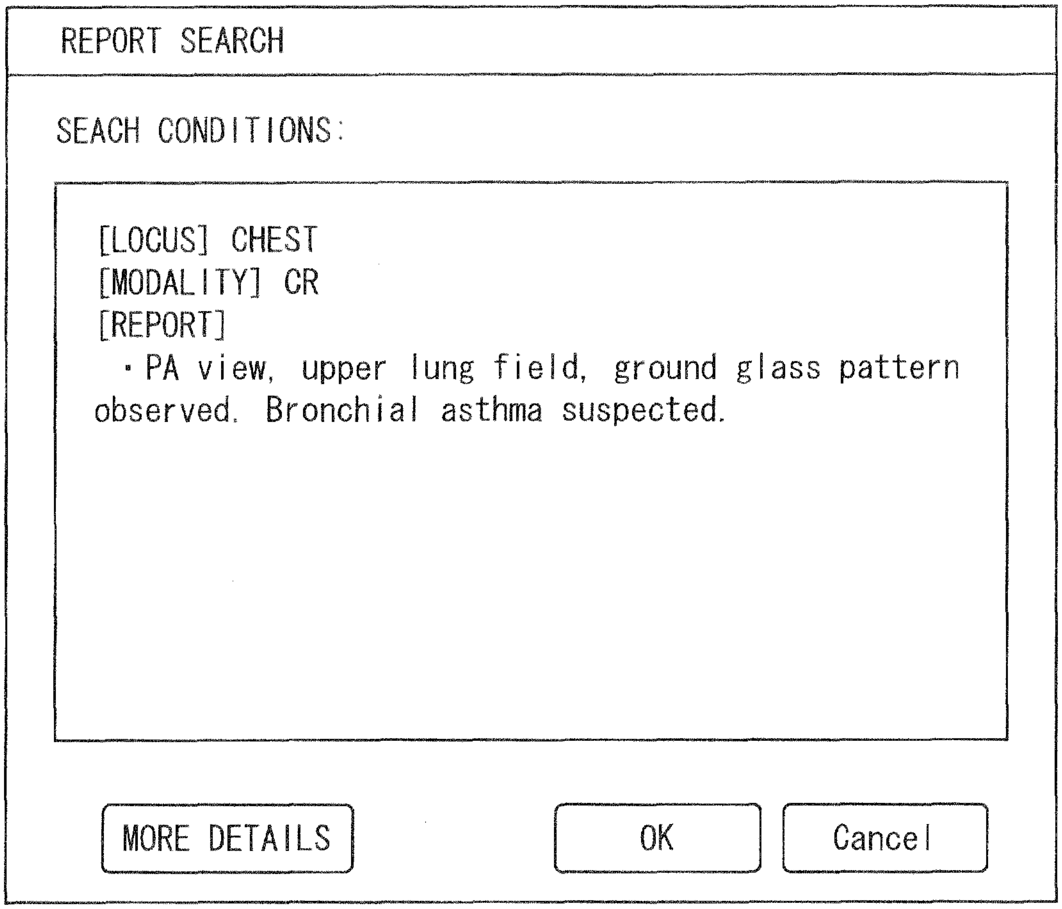
FIG. 7 A diagram showing a dialog box for confirmation of a search query.

A specific definition of this matching degree, and an algorithm of a report search based on such a matching degree will be described with reference to FIGS. 7 to 11. For example, a case where the user applies the query "PA view (PA: posteroanterior view), upper lung field, ground glass pattern observed. Bronchial asthma suspected." as the search query 300 shown in FIG. 4 is assumed. In this case, for the finding report search query 311 extracted based on this search query 300, a dialog box of the search items included therein is expressed as shown in FIG. 7. If the structured report of FIG. 9 and the structured report of FIG. 11 corresponding to the contents of FIG. 8 and FIG. 10, respectively, are found in the imaging test report DB 240 as a result of the search based on the finding report search query 311, both of them are extracted as a search result. Here, in FIG. 9 corresponding to FIG. 8, one sentence includes all of query words (keywords) serving as the search items, while in FIG. 11 corresponding to FIG. 10, a first sentence includes "PA view", "upper lung field", and "stripe", a second sentence includes "PA view", "middle lung field", and "ground glass pattern", and a third sentence includes "bronchial asthma". Thus, as a whole, each of the reports of FIG. 8 (FIG. 9) and FIG. 10 (FIG. 11) includes all of the query words shown in FIG. 7. The report of FIG. 8 (FIG. 9) and the report of FIG. 10 (FIG. 11) is different from each other in that, in the report of FIG. 8 (FIG. 9), all of the query words are included in one sentence while in the report of FIG. 10 (FIG. 11), the query words corresponding to the interpretation result are divided into a plurality of sentences.

Figure 10:
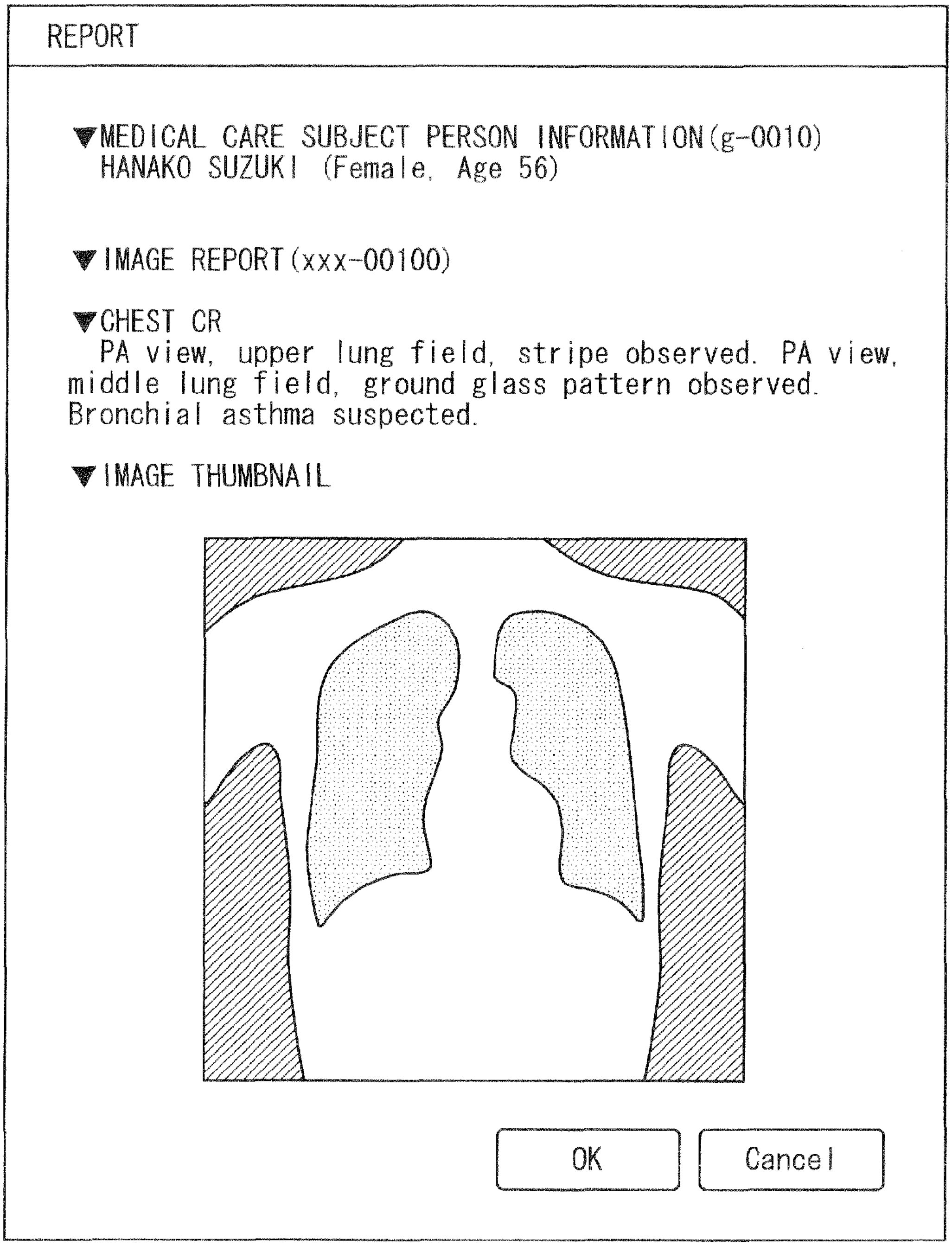
FIG. 10 A diagram showing an example of another finding report existing in the imaging test report DB.

In a case where such a structured report is used as the search object and the search is performed based on the query 311, both of the report of FIG. 8 (FIG. 9) and the report of FIG. 10 (FIG. 11) are hit in a search result. Here, it is considered that the report having all the search words included in a smaller number of sentences is more relevant. In this case, the matching degree of the report of FIG. 8 (FIG. 9) is set higher than the matching degree of the report of FIG. 10 (FIG. 11). A report having all the query words included in one sentence has the highest matching degree. As a method for calculating the matching degree based on such a point of view, various methods are conceivable. For example, the matching degree may be set to be the inverse of the number of sentences across which the query words are distributed.

By performing the above-described process, a result matching the finding report search query 311 of FIG. 3 is extracted independently of the search of the specimen test, and additionally, a report search result 331 assigned with the matching degree rated as a numerical value is also obtained. Such a "matching degree" represents the degree of matching with the search item designated by the user. In a more general sense, the matching degree is an indicator value representing the value of the individual database as a search result, that is, the matching degree belongs to a concept of "individual score". Accordingly, the report search result 331 assigned with the matching degree is dealt with as a report search result 341 with the individual score attached.

<1-2-3. Algorithm of Specimen Test Search>

Next, an algorithm of the specimen test search will be described with reference to FIG. 12. Various methods may be used for searching the specimen test alone. Among them, in this embodiment, a method requiring a relatively low cost for calculation will be shown.

This embodiment focuses on an abnormality flag included in the specimen test. The abnormality flag is one of items included in the test result. An actual test value is compared with a normal value range derived from the sex and the age of the medical care subject person. If the test value is beyond the normal value range, either one of flags "above normal value" ("ABNORMAL VALUE (HIGH)") and "below normal value" ("ABNORMAL VALUE (LOW)") is given. Here, the search is performed in accordance with a pattern of the abnormality flag. That is, a plurality of test items and whether the values thereof are "normal value". "abnormal value (high)", or "abnormal value (low)" are designated as a search query corresponding to the specimen test query 312. A search result matching the pattern thereof is obtained (see FIG. 12).

In the search of the specimen test, too, the individual score (or the matching degree representing the degree of matching with the search item) can be assigned. For example, in the aforementioned example, in a case where the search query includes four items A to D (see FIG. 12A), it is natural to consider that matching all of the four conditions has a higher matching degree. Even if only three of the items are matched, presenting this search result to the user instead of discarding it as being mismatched can contribute to prevention of missing of important information. The items of the query are searched in the OR search, and the ratio of items matching the search items is set as the individual score. For example, in a case where three items among the four items of the search query are matched, the individual score is set to be ¾=0.75 (see FIG. 12B), and in a case where all the items are matched, the individual score is set to be 4/4=1.0 (see FIG. 12C).

By performing the above-described process, a result matching the specimen test in a flow of FIG. 3 is independently extracted, and at the same time, a search result 332 assigned with the matching degree, that is, a search result 342 with the individual score attached, is obtained (step S4).

<1-2-4. Algorithm for Pairing of Individual Search Result>

Then, in step S5 of FIG. 3, the search result pairing section 25 performs a process for associating the report search result 341 with the specimen test search result 342. This process corresponds to a process for combining individual search results extracted from a plurality of databases and thereby generating a combined search result.

Figure 13:
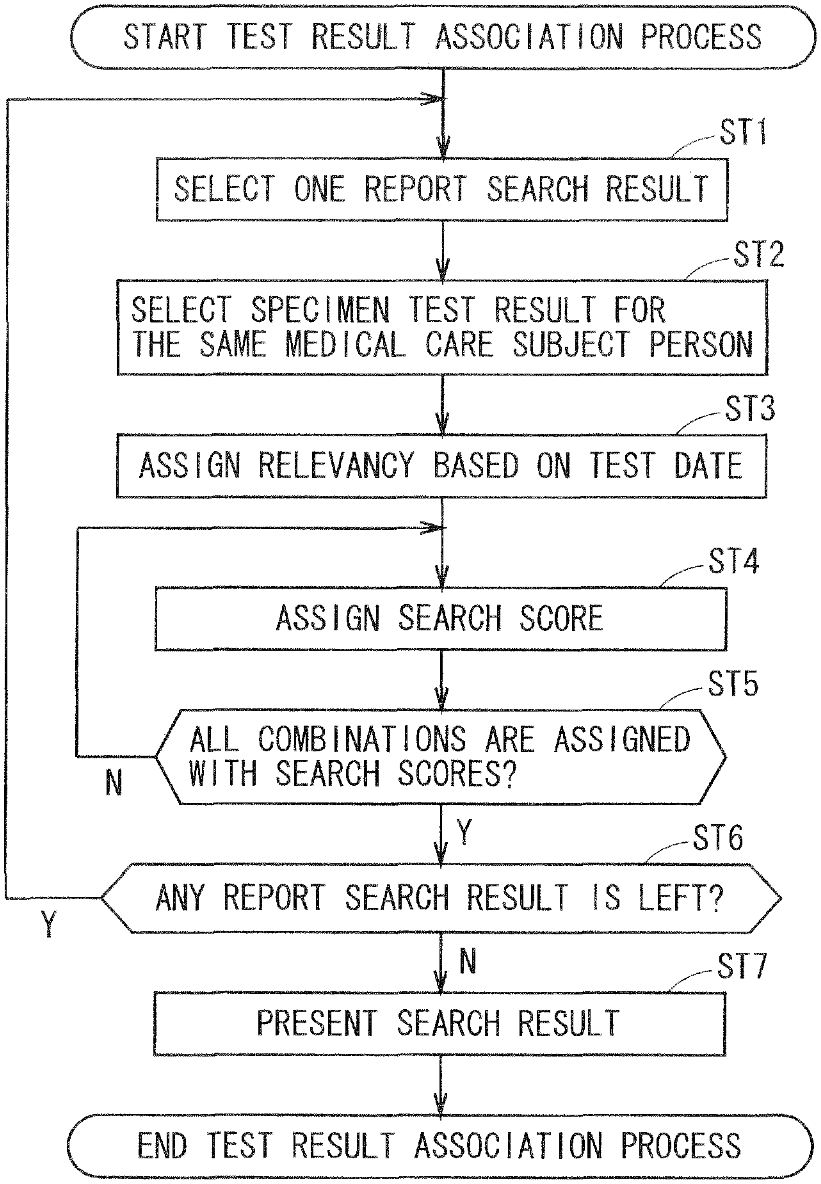
FIG. 13 A flowchart illustrating a search-result association operation.

FIG. 13 is a flowchart showing a search-result association operation. The association of the individual search results is performed in the process steps which will be described below with reference to FIG. 13.

Firstly, in step ST1, one search result is selected from the report search result 341 of FIG. 3. The order of this selection is not particularly limited. For example, the selection may be made in chronological order of hitting in the search. The report search result 341 selected at this time is defined as a report SR(i). Then, in step ST2, a specimen test result for the same medical care subject person as the medical care subject person of the report SA(i) selected in step ST1 is selected from the specimen test search result 342 of FIG. 3. This can be performed by checking the medical care subject persons ID included in the respective search results against each other. The selected specimen test search result of the same medical care subject person as that of the report SA(i) is defined as a search result SB(i.k). The former argument "i" indicates that the medical care subject person of the test result is the same as that of the report SA(i). The latter argument "k" is an indicator for distinguishing a plurality of specimen test search results from one another, in consideration for a case where the plurality of specimen test search results are obtained with respect to the medical care subject person. If only one specimen test search result is obtained with respect to the same medical care subject person, k=1 is established.

Then, in step ST3, a relevancy score (which will be described later) based on the date is assigned to a combination of the selected report search result SA(i) and specimen test result SB(i.k). Then, the product of the relevancy score obtained in step ST3 and the individual score (matching degree) for the report search result SA(i) and the specimen test result SB(i.k) is assigned, as a final search score, to the combination (step ST4). While changing the argument k of the specimen test result SB(i.k), the above-described routine is repeated until all combinations of (i, 1), (i, 2), . . . are assigned with search scores (step ST5). Moreover, similarly, while changing the argument i of the report search result SA(i), steps ST1 to ST5 are repeatedly performed on all the report search results (step ST6). Finally, a plurality of combinations of search results "SA(i)+SB(i.k)" are, together with the search scores thereof, stored as the combined search result in a storage section within the client terminal 101, and additionally displayed on the display 101*b* (step ST7). If no specimen test result SB(i.k) having the same medical care subject person ID as that of the report search result SA(i) exists in the database, no combined search result is displayed for that medical care subject person.

Figure 14:
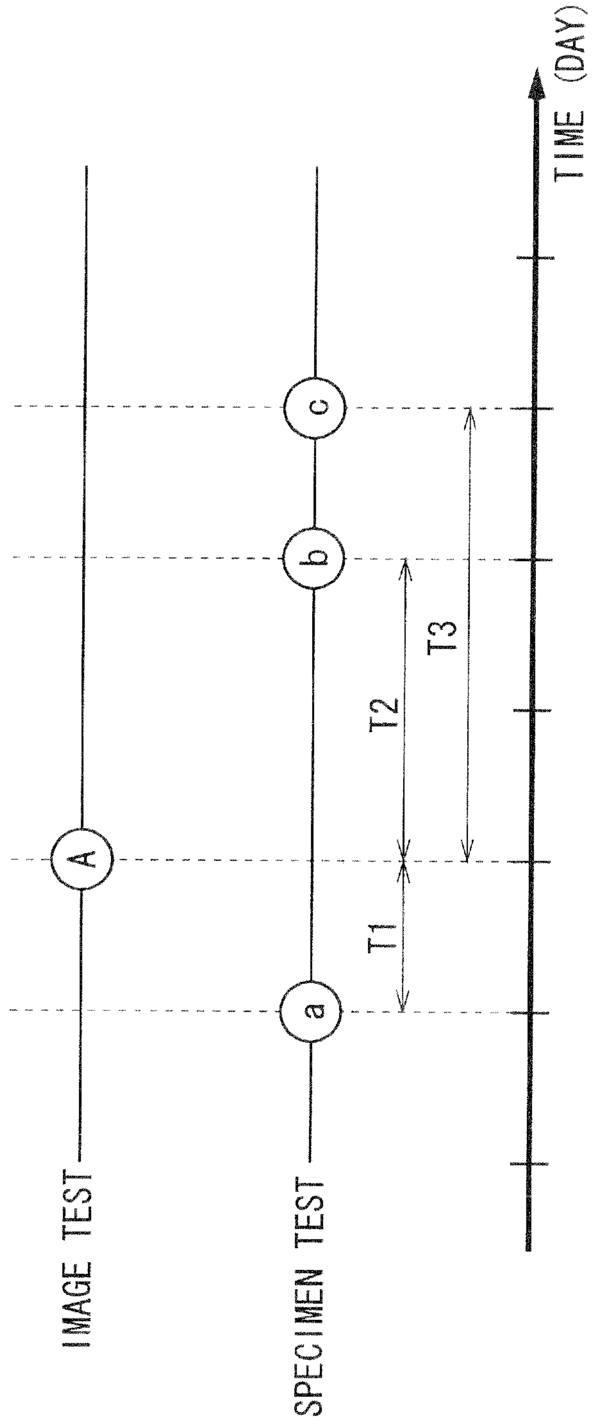
FIG. 14 A diagram explaining an algorithm for combining search results.

FIG. 14 is a diagram explaining an algorithm of combining individual search results. A more specific description will be given to the relevancy score based on the date with reference to FIG. 14.

Firstly, scoring is performed based on the degree of temporal separation (temporal distance) between the time and date of the imaging test and the time and date of the specimen test. For an accurate comparison, it is preferable to consider not only a difference in the test date but also a difference in the test time. However, in the whole of the medicine tests, a situation where the same test is repeatedly performed on the single medical care subject person in one day does not often occur. Therefore, in many cases, it suffices that the difference in the test date is considered as the minimum information. Thus, in this embodiment, the inverse of the degree of separation of the date is adopted as an index number Da indicating the closeness of the dates, and used as the relevancy score. In a case shown in FIG. 14, since a distance (T1) between the imaging test A and the specimen test a is one day. Da=1/1=1 is established. Since a distance (T2) between the imaging test A and the specimen test b is two days, Da=1/2=0.5 is established. Since a distance (T3) between the imaging test A and the specimen test c is three days, Da=1/3=0.3 . . . is established. In FIG. 14, the imaging test A corresponds to the report search result SA(i) already described, and the specimen tests a, b, and c correspond to the specimen test results SB(i.k): k=1, 2, and 3.

Then, the product of the relevancy score obtained at this time and the individual score (individual matching degree) of each specimen test is set as a final search score.

This enables the user to obtain several combinations S of the finding report and the specimen test for a common medical care subject person (the combined search result 350 in FIG. 3). These combinations are assigned with the search scores that are based on the matching degree in the individual search and the degree of separation of the date, and the search results are displayed on the display 101*b* in descending order of the score (step S6). The user can rely on the score in viewing the results.

The finding report has attached thereto an image ID serving as test-image-specific information. In the example of FIG. 8, the image ID is "image id="1072"", and in the example of FIG. 9, the image ID is "image id="5658"". These image IDs concern, among the imaging test results (digital images) stored in the imaging test result DB 220, imaging test results based on which the finding reports are generated. Accordingly, these imaging test result can be identified based on the finding reports extracted by the search.

1-3. Operation Procedure of User

Hereinafter, with reference to FIGS. 15 to 24, a description will be given to how the user utilizes the medical information system 1 of this embodiment, and particularly to an example of an operation procedure on a GUI.

<1-3-1. Data Saving>

Figure 15:
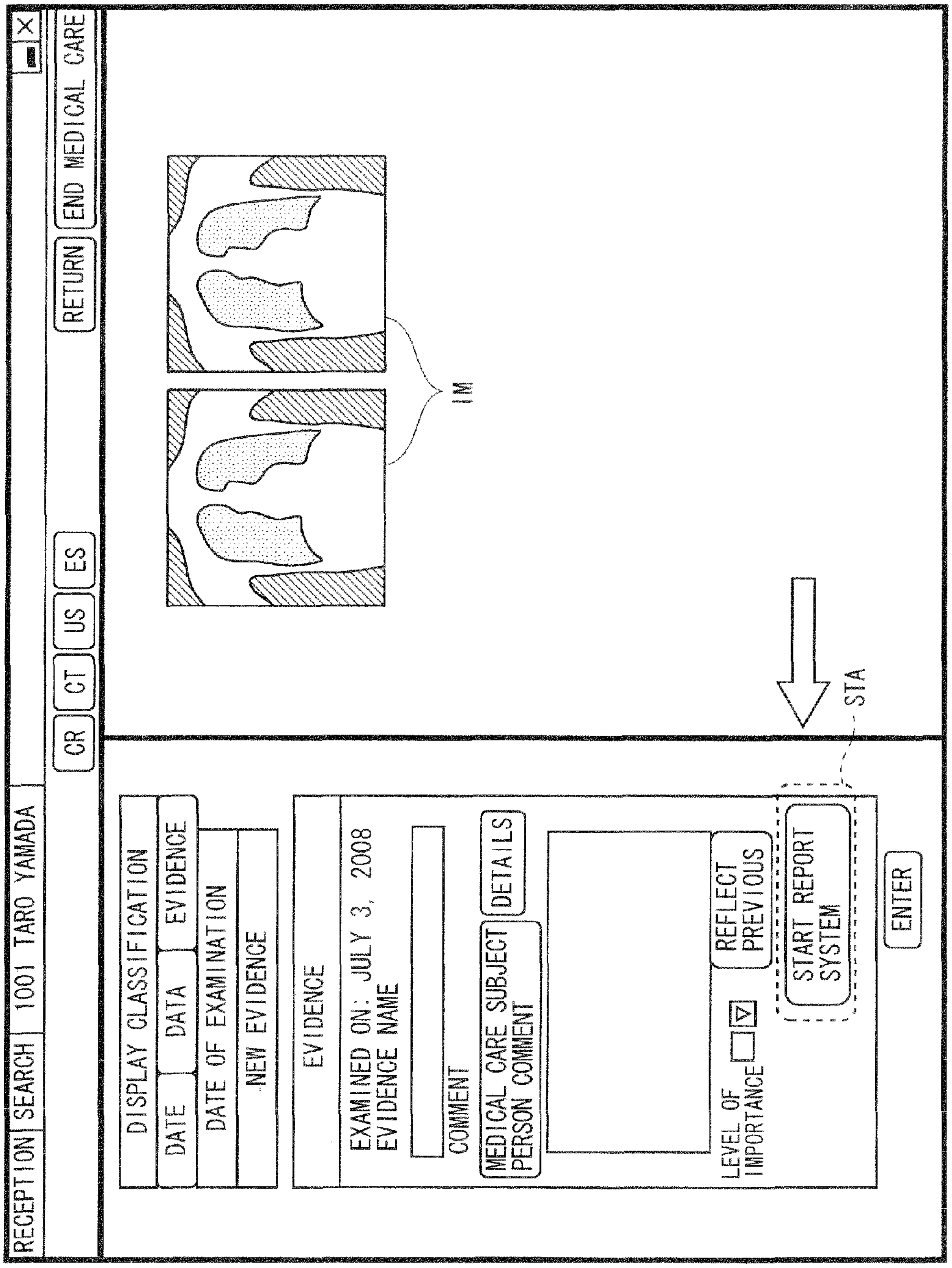
FIG. 15 A diagram showing an example of client software in a chest CR test.

Prior to examining the medical care subject person (or after the examination), the user (doctor) performs a necessary clinical test by himself/herself, or alternatively orders a test. A test result for this medical care subject person is digitally inputted through the modality terminal 102, or manually inputted through the client terminal 101. Thereby, the test result is imported into the medical information system 1 and saved. By using the client software, the test result is displayed on the display 101*b* of the client terminal 101. FIG. 15 is a diagram showing an example of a display in a chest CR test. As shown in FIG. 15, two thumbnail images IM of the chest CR are displayed on a screen of the display 101*b*.

Figure 16:
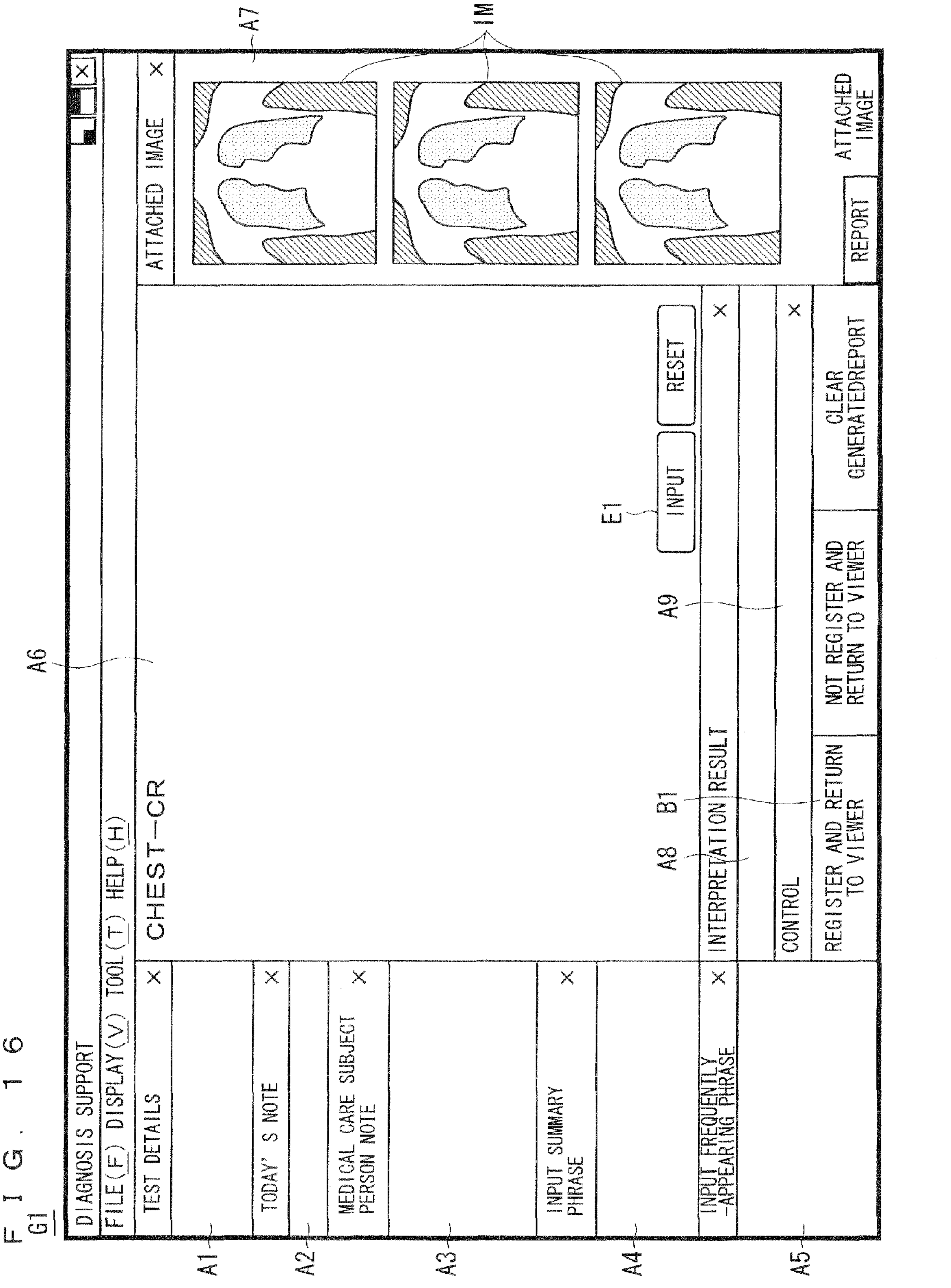
FIG. 16 A diagram showing an example of a screen of a report system.

Here, the doctor can start up a report system by pressing a button STA of "START REPORT SYSTEM". FIG. 16 is a diagram showing an example of a screen G1 of the report system. As shown in FIG. 16, the screen G1 of the report system mainly includes:

- an area (test information area) A1 for test details;
- an area (today's note area) A2 for a note of a medical treatment and the like of that day;
- an area (medical care subject person note area) A3 for a note concerning a medical care subject person;
- an area (summary phrase input area) A4 for input of a summary phrase;
- an area (frequently-appearing phrase input area) A5 for input of a frequently-appearing phrase;
- an area (report generation area) A6 for generation of a finding report;
- an area (image attachment area) A7 for attachment of representative images IM;
- an area (interpretation result display area) A8 for display of an interpretation result; and
- an area (command input area) A9 for listing icons for input of a command.

For example, on the screen G1 (FIG. 16) of the report system:

- in the test information area A1, the attribution information according to the medical care subject person and the test is displayed (FIG. 17A);
- in the today's note area A2, a note concerning the diagnosis information of that day is displayed (FIG. 17B);
- in the medical care subject person note area A3, a note concerning symptoms of the medical care subject person, etc. is displayed (FIG. 17C);
- in the summary phrase input area A4, a brief sentence as a summary is displayed (FIG. 17D); and
- in the frequently-appearing phrase input area A5, frequently used words are displayed (FIG. 17E).

FIG. 18 is a diagram showing an example of a display of an input-support template display TP. As shown in FIG. 18, the input-support template display TP is displayed in the report generation area A6. Candidate words are displayed for each of the groups mentioned above. The candidate word is clicked on for selecting a word to form a sentence. Finally, a button E1 of "INPUT" (FIG. 18) is pressed, so that a natural sentence can be automatically generated. Here, clicking on "REGISTER AND RETURN TO VIEWER" B1 (FIG. 16) allows the generated sentence to be registered as a finding report for the current test. In the imaging test report DB 240, the generated report is described using structured document data such as the RDF (Resource Description Framework), and registered. In this manner, the finding report corresponding to the imaging test is added to and accumulated in the imaging test report DB 240.

<1-3-2. Search Operation>

Figure 19:
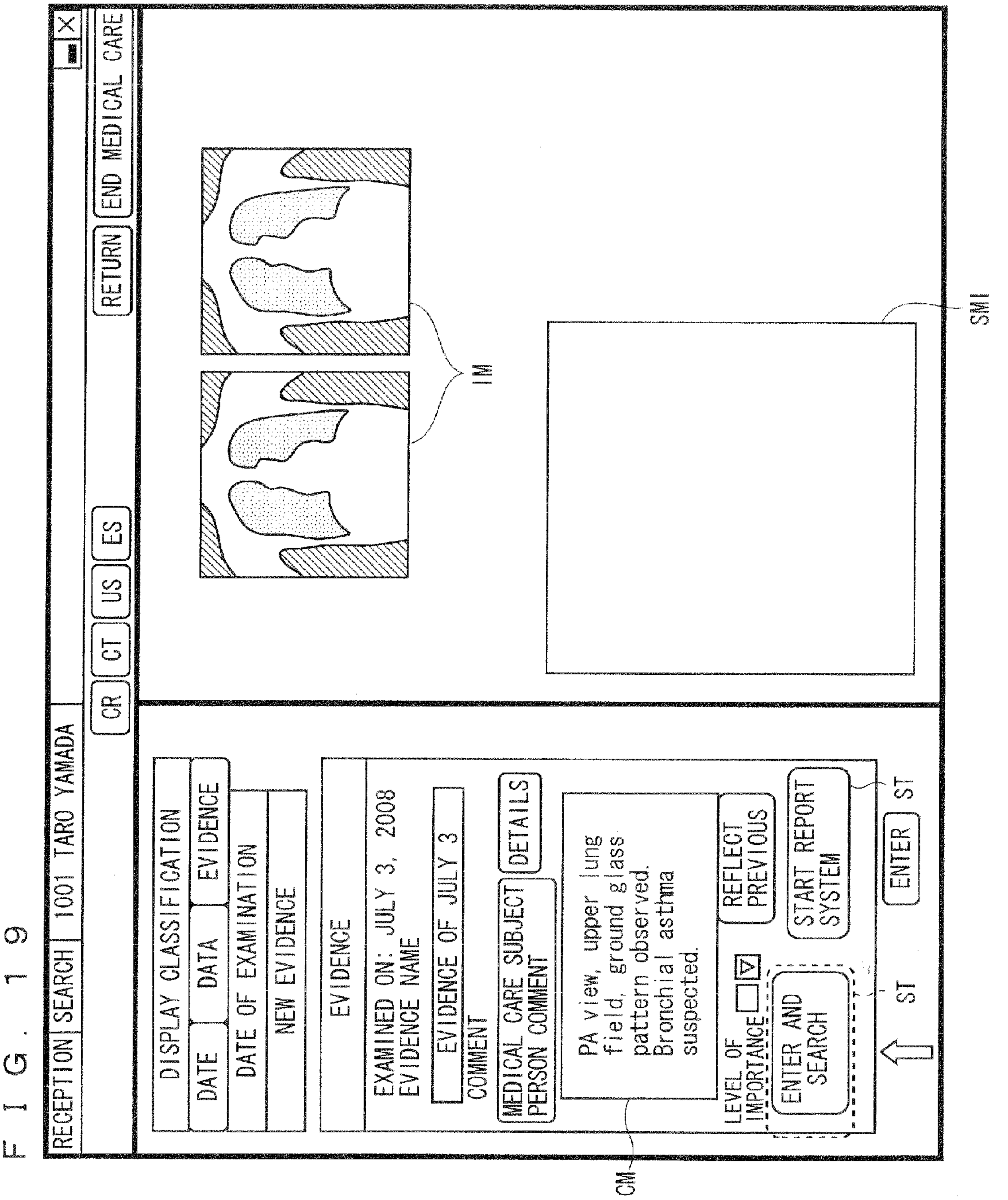
FIG. 19 A diagram for explaining a display of results of an imaging test and a specimen test on the client software.
Figure 20:
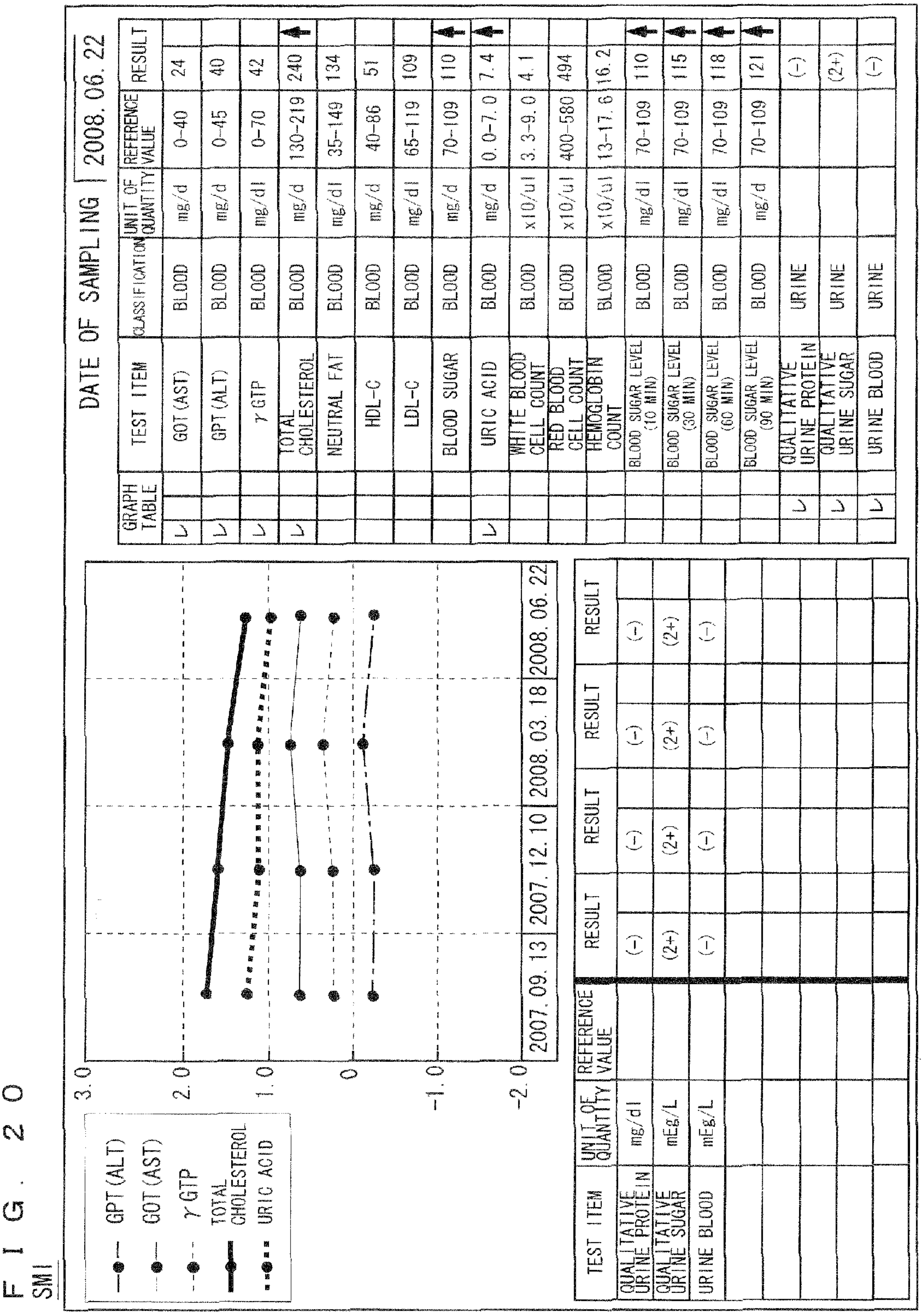
FIG. 20 A diagram showing an example of a specimen test result.

Next, a situation where the search is performed will be described. The doctor can view several test results together on the display 101*b* of the client terminal 101. FIG. 19 is a diagram schematically showing a situation where chest CR images IM and a specimen test result SMI are displayed on the display 101*b*. FIG. 20 is a diagram showing an example of details of the specimen test result SMI. It is to be noted that a finding report CM generated through the above-described procedure is given to the chest CR test as shown in FIG. 19. Here, a test similar to a collection of tests that are currently opened is searched for.

Figure 21:
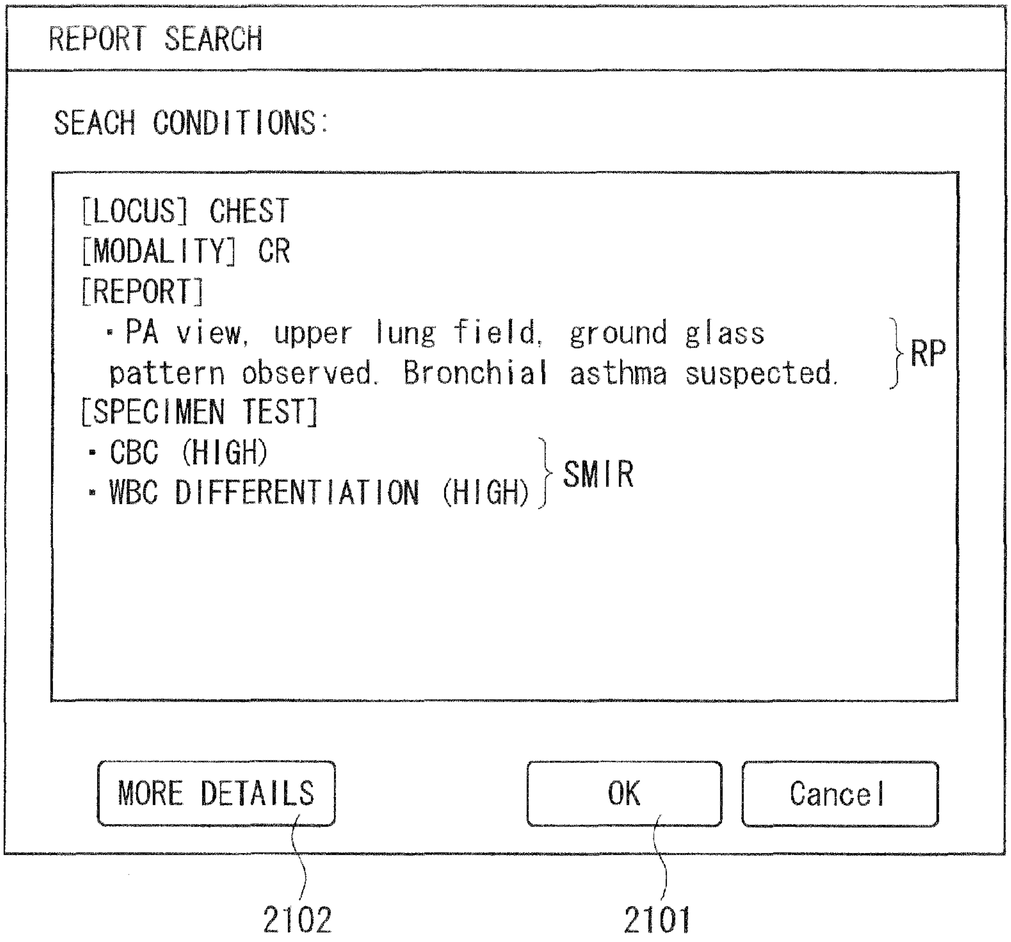
FIG. 21 A diagram showing a dialog box for confirmation of a search query at a time of similarity search.

Firstly, a button ST of "ENTER AND SEARCH" (FIG. 19) located at a lower left portion of the screen is pressed. Thereby, a dialog box for confirmation of a search query is displayed as shown in FIG. 21. This shows a search query in a case of a similarity search. In a report area RP (FIG. 21), a medical care subject person comment CM (FIG. 19) given to the imaging test of FIG. 19 is displayed as a search query. Additionally, contents in a specimen test area SMIR (FIG. 21) are illustrated. Here, ones of the blood test results indicating that the abnormality flag is abnormal are displayed as a query.

Figure 23:
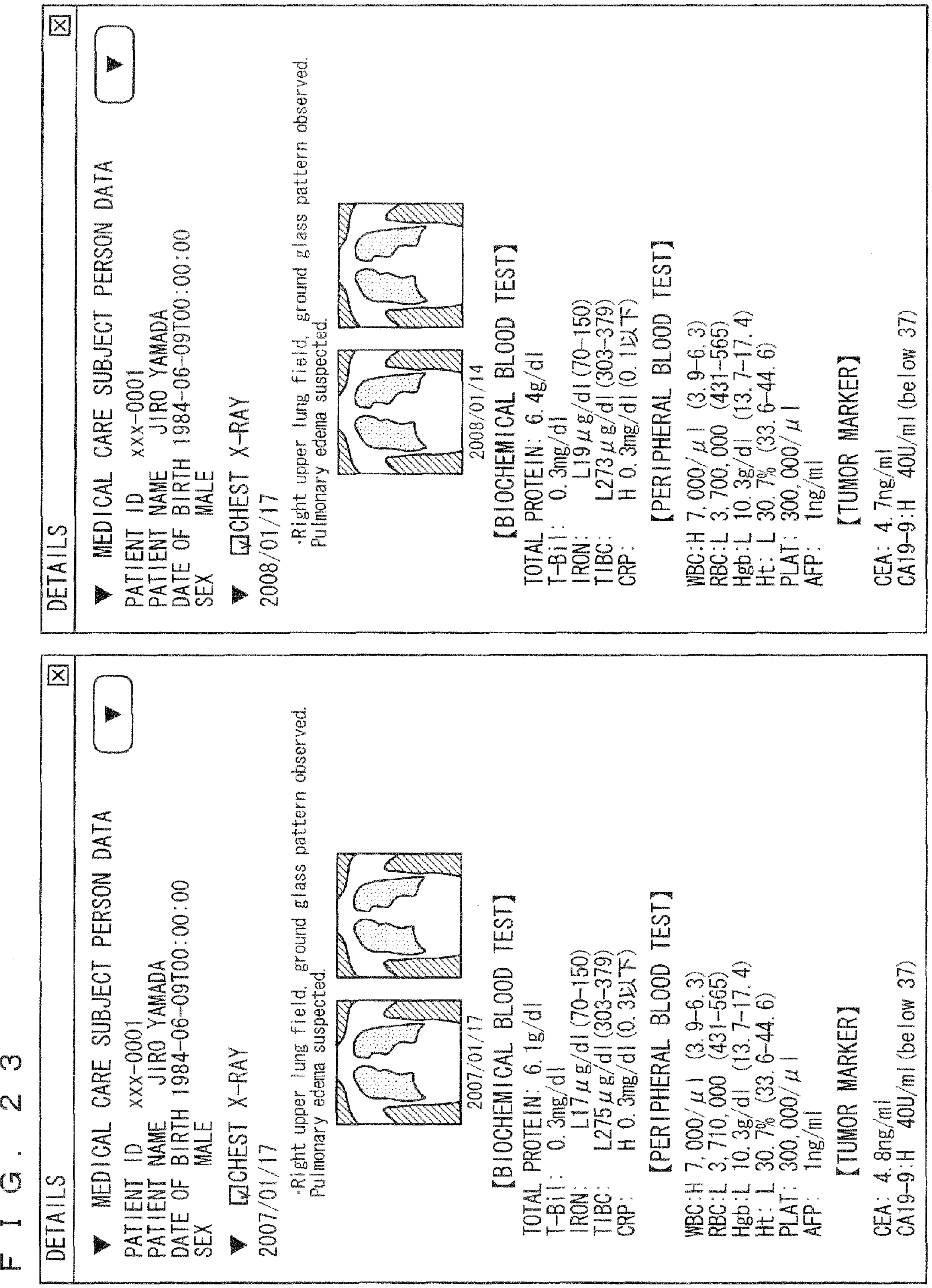
FIG. 23 A diagram showing an example of a dialog box presenting details of the search result.

If an OK button 2101 (FIG. 21) is pressed in this state, a search is performed under search conditions of FIG. 21, and search results are displayed as shown in FIG. 22. These search results are obtained by the routine described with reference to FIG. 3 and subsequent FIGS. In the search results, a plurality of kinds of search results are arranged in the order of the search score. In each record (line), a report ID identifies a finding report of the imaging test, and identifies a specimen test result such as the CBC and the WBC differentiation. Since the finding report of the imaging test and the image data in the imaging test result DB 220 are linked by the image report ID, the image data is indirectly included in the combination of the finding report and the specimen test result for the same patient. The doctor double-clicks on a result of interest, and thereby views detailed information. FIG. 23 is a diagram showing a dialog box presenting the search result. As shown in FIG. 22, two results may be displayed for comparison.

On the other hand, a button 2102 of "MORE DETAILS" (FIG. 21) is clicked on, a dialog box allowing the search query to be modified is opened as shown in FIG. 24. Thus, the user can modify the query and start a new search.

2. Second Embodiment

A configuration of a medical information system according to a second embodiment is identical to that of the first embodiment shown in FIG. 1 in terms of hardware, and is also substantially identical to that of the first embodiment shown in FIG. 1 in terms of functions, except that in the second embodiment, the finding report is a report not only on the imaging test but also on a collection of several tests (hereinafter simply referred to as "test set"). Thus, in a medical information server 200A according to the second embodiment shown in FIG. 24, the parts identical to those of the medical information server 200 according to the first embodiment are denoted by the identical reference numerals, without giving their descriptions below. In the following, only the points different from the medical information server 200 according to the first embodiment will be described.

The medical information server 200A according to the second embodiment is different from the medical information server 200 shown in FIG. 2, in that a test set DB 2301 is additionally provided so that a report is made on the test set. The test set DB 2301 stores test combination information that indicates which tests the report has been made on. Actually, in a user's operation, with respect to a single diagnosis subject, an imaging test result stored in the imaging test result DB 220 and a specimen test result stored in the specimen test result DB 230 are recalled and displayed on a single screen of the display 101*b* of the client terminal 101, and a sentence of the report is inputted. A digital file of this report is stored in a report DB 2302, and at the same time, association information (relation information) is saved in the test set DB 2301. The association information indicates the imaging test result and the specimen test result that form the basis for the diagnosis in the report. The test set DB 2301 is one aspect of a set information database that stores information identifying a set of a plurality of kinds of medical data. Accordingly, by repeating such a saving, a combination of three kinds of information, namely, "report+imaging test result+specimen test result" can be recognized by referring to the contents of the test set DB 2301.

Figure 26:
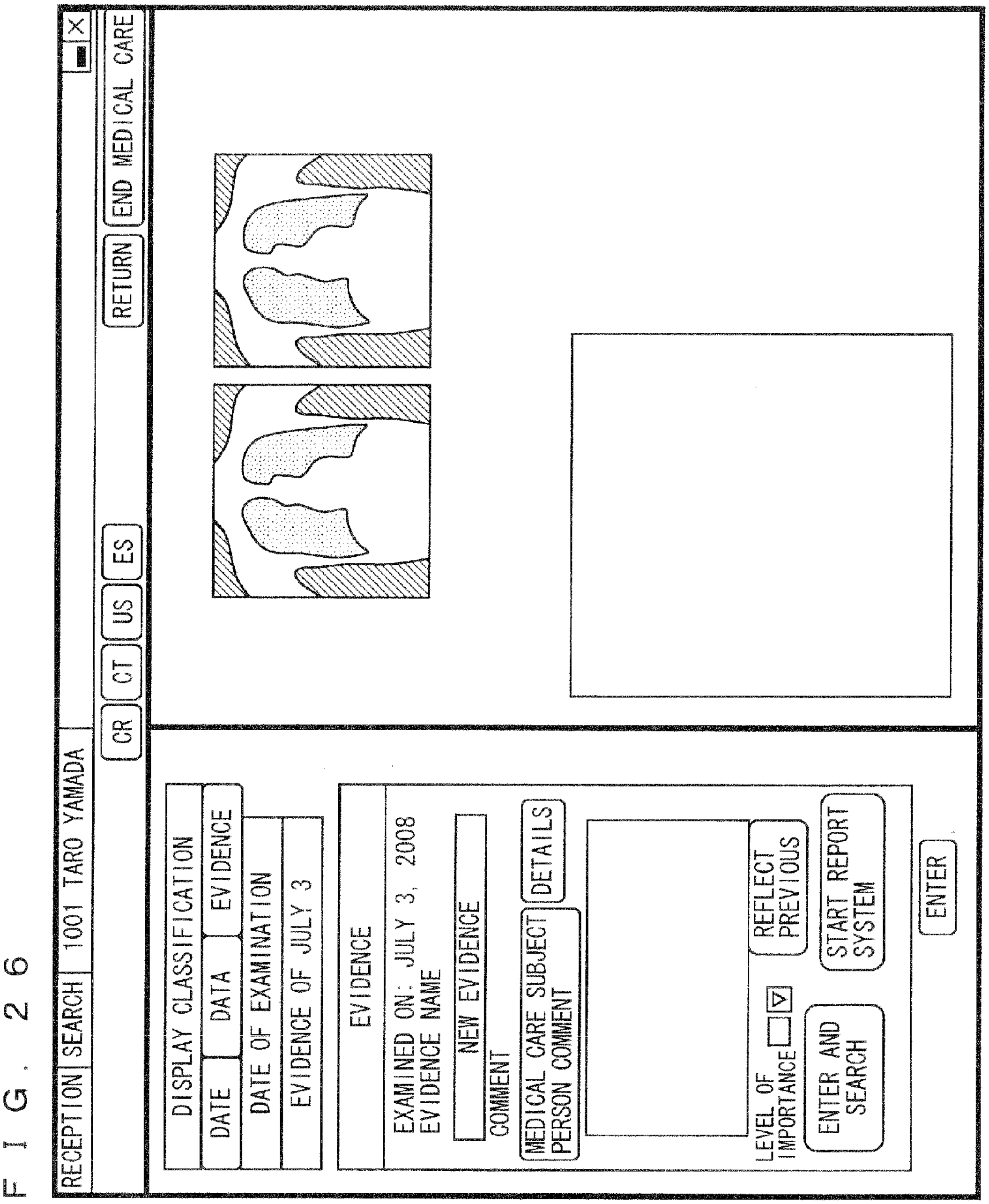
FIG. 26 A diagram showing an example of client software according to the second embodiment.

FIG. 26 is a diagram showing an example of a display made on the display 101*b* at a time of generating a report in the second embodiment. FIG. 26 is different from FIG. 15, in that the imaging test result and the specimen test result are displayed together. In a case where a report is generated in this state, the imaging test result and the specimen test result are registered as a test set.

Figure 27:
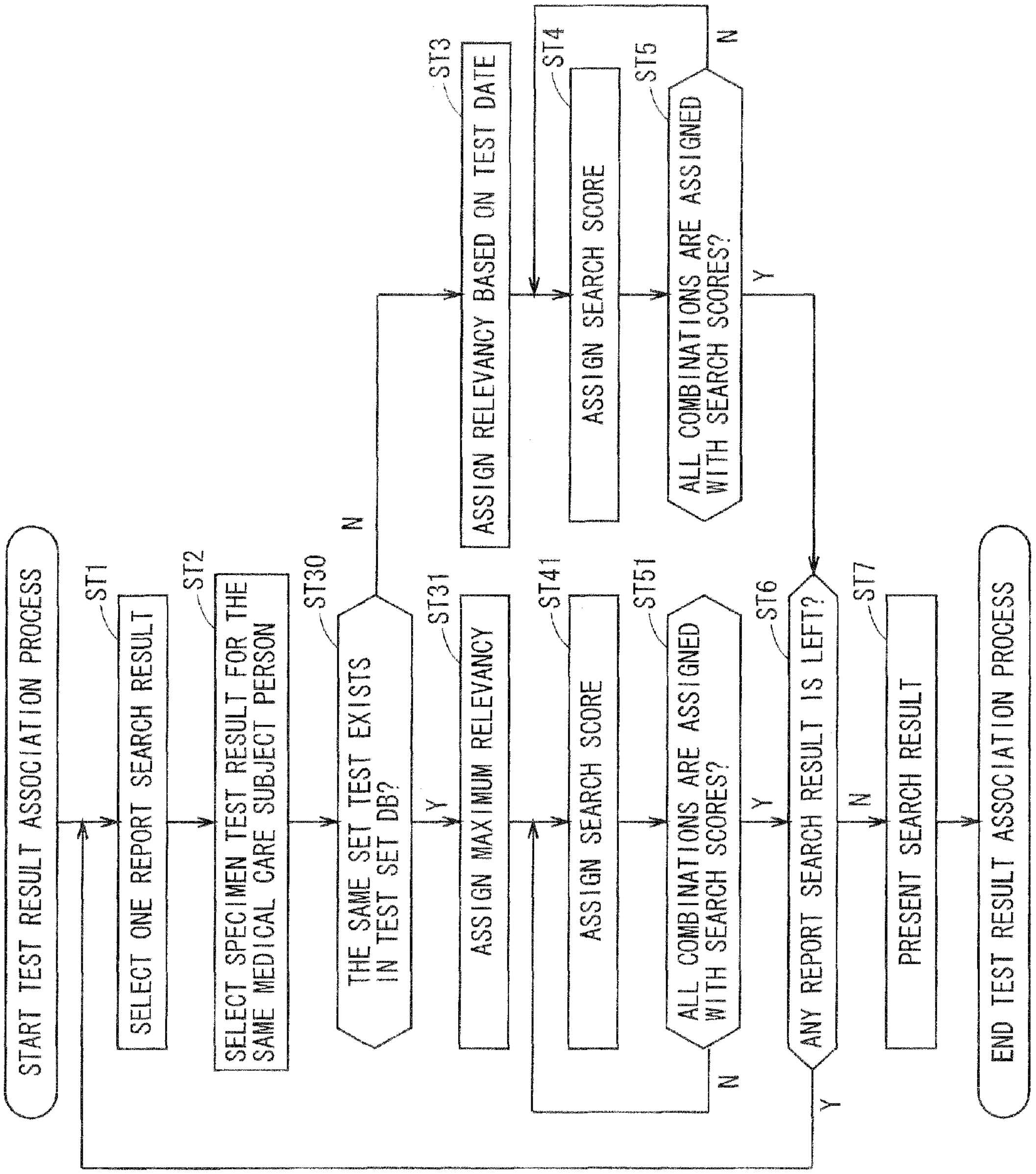
FIG. 27 A flowchart illustrating a search-result association operation according to the second embodiment.

FIG. 27 is a flowchart showing a process of associating search results in the second embodiment. A search algorithm of the second embodiment is basically the same as that of the first embodiment. Therefore, a description will be given with a focus on the unique associating process with reference to FIG. 27. The parts common to FIG. 13 are denoted by the same reference numerals.

Similarly to the first embodiment, in steps ST1 and ST2, a combination of a report search result and a specimen test result are extracted as data matching the search query. In step ST30, the test set DB 2301 is referred to for the test set information, and thereby whether or not the report search result and the specimen test result in the combination is included in the same test set is determined. If they are included in the same test set, the maximum relevancy score is assigned (step ST31). If they are not included in the same test set, similarly to the first embodiment, a relevancy score based on the test date is assigned to the combination of the report search result and the specimen test result selected in step ST1 and ST2 (step ST3). Subsequently, the same steps as those of the first embodiment are performed (steps ST4 to ST7).

In a case of going through step ST31, the product of the relevancy score obtained in step ST31 and the matching degrees (individual scores) obtained by the routine of FIG. 3 are set as the final search score and assigned to the combination (step ST41). This process is repeated until the search scores are assigned to all the combinations (step ST51). Steps ST6 to ST7 are identical to those of the first embodiment.

Through the above-described process, tests for which the doctor has explicitly written a finding as one set can be preferentially extracted as strongly relevant tests, irrespective of the test date. The usefulness thereof is particularly enhanced in a case of an application to a medical information database system having a CR (X-ray image digitalizer) console function and a viewer/filing function being integrated with each other.

3. Third Embodiment

A medical information system according to a third embodiment is different from that according to the first embodiment, in that "sex" and "age" are newly added to the search conditions.

FIG. 27 shows a dialog box for confirmation of a search query in the third embodiment, which corresponds to that after the button SC of "ENTER AND SEARCH" is pressed in the first embodiment (FIG. 19). FIG. 27 is different from FIG. 19, in that "SEX SE" and "AGE AG" are added to the search conditions. The sex SE and the age AG mean that the sex and the age of the medical care subject person displayed in FIG. 21 are added to the search query.

As described above, in a case of searching for medical care test information including a plurality of kinds of test results, only a test result of a medical care subject person corresponding to the sex and the age is set as a search object to be searched for. This refines the search conditions and enables a more accurate search.

4. Modification

In addition to the above-described embodiments, the present invention may be modified as follows. The embodiments and the following modification can be combined as long as no technical inconsistency arises.

As a search logic in each database, the technique disclosed in Japanese Patent No. 4191762 is applicable. To be specific, each time a new search is performed by the user, a system memorizes and analyzes which of a plurality of kinds of extracted data the user focuses on (refers to details thereof), and updates a search logic in accordance with a result of the analysis.

For example, a case is assumed in which, when a search query includes "lung" and a plurality of finding reports relevant to "lung" are extracted, a doctor that is the user often refers to details of a finding report that also includes the word "recurrence". In this case, the search logic of the system can be developed such that, when the doctor designates "lung" in a search query, the individual score of a finding report that also includes the word "recurrence" can be made higher. Moreover, in a possible application, for example, in a case where the system coordinates also with a medical paper database, information about a new arrival paper including both of the words "lung" and "recurrence" is displayed as a hyperlink in a part of a search result screen.

In the above-described embodiment, the phrase "medical care subject person" is used based on the assumption that a medical care subject person individual is human. However, the phrase "medical care subject person animal" is also acceptable.

In the medical information system of the above-described embodiment, for example, a medical receipt system may be provided. That is, if a receipt DB indicating a kind of medical treatment performed on a medical care subject person who was a test object and medical costs resulting therefrom is extracted together with a report and a test result, review can be made in terms of the medical costs, too.

In the above-described embodiment, the server and the client terminal are separate machines, but this is not limitative. Information processing functions of the system of the present invention may be installed on the same machine.

In the structured-document of the above-described embodiment, a prefix or a suffix may be attached. For example, the prefix "left" may be added to "upper lung field" to result in "left upper lung field".

In the pairing of the individual search results in the above-described embodiment, the inverse of the degree of separation between the time and date of the imaging test and the time and date of the specimen test is adopted as the index number Da indicating the closeness of the dates, and set as the relevancy score. Here, the index number Da may be any function instead of the inverse of the difference in the date, as long as in the function, the index number Da increased as the time and date of both tests get closer to each other.

In the algorithm of the above-described embodiment, filtering based on the following items enables computation for data extraction to be efficiently performed and additionally prevents a situation where a excessive amount of information is extracted from the respective databases to confuse the user. Particularly in a case of a large-scale database, an enormous amount of test results are accumulated, and therefore the filtering (refining) based on the following items is helpful.

To be specific, a threshold value for determination is set on each of items mentioned later, and in a case where the threshold value for determination is set as the lower limit, data having an index number for determination lower than the threshold value for determination is excluded from the objects to be extracted; and in a case where the threshold value for determination is set as the upper limit, data having an index number for determination higher than the threshold value for determination is excluded from the objects to be extracted.

(1) In the extraction of the result of the search for the finding report:

the index number for determination=the matching degree (individual score) of the finding report with the report search query; and the threshold value for determination=the lower limit of the matching degree.

(2) In the extraction of the specimen test result corresponding to the finding report:

the index number for determination=the date difference between the date of the finding report (imaging test) and the test date of the specimen test; and the threshold value for determination=the upper limit of the date difference.

(3) In the selection of the specimen test result:

the index number for determination=the matching degree (individual score) of the specimen test result with the specimen test search query; and the threshold value for determination=the lower limit of the matching degree.

(4) In the selection of the combination of the plurality of relevant tests:

the index number for determination=the relevancy score; and the threshold value for determination=the lower limit of the relevancy score.

(5) In the identification and display of the final search result:

the index number for determination=the relevancy score; and the threshold value for determination=the lower limit of the relevancy score.

In one search, the number of search items in the query (denominator) is constant. Therefore, setting the individual score to be the ratio of the medical data items that match the search items to the number of search items in the query is equivalent to setting the individual score based on the absolute number of medical data items that match the search items.

Each of the search items in the query may be weighted in accordance with the level of importance. In this case, instead of a binary manner of whether or not each search item is matched, the individual score is calculated with adding a weight in accordance with the degree of matching. For example, the system may be configured as follows. That is, in a case where a test item P is specific to a certain disease (that is, an abnormal value often appears in the disease but scarcely appears in other diseases) while appearance of an abnormal value in another test item Q is not specific to the disease (that is, an abnormal value often appears in other diseases, too), the doctor who performs the search designates the test item P as "important" by operating the operation input section 101*a* of the client terminal 101. Thereby, the extraction process is executed with a higher individual score being assigned to a test result in which the test item P takes an abnormal value than to a test result in which the test item Q takes an abnormal value.

The plurality of databases may include databases of not only the test diagnosis information and the patient information but also nursing care data, electronic medical chart information, medical papers, pharmacological information, side-effect information, and the like. Among them, the nursing care data is digital information recording nursing activities of the nurse, and the electronic medical chart information is digital information of a record of medical cares made by the doctor. Thus, the present invention is directed to general medical data, and applicable to various medical information systems.

In the above-described embodiment, the test date is used as the indicator for obtaining the relevancy score. In general, not only a "test identification date" which means the test date, but also a date on which a specimen is obtained, a date on which test data is inputted, and the like, may be used.

DESCRIPTION OF THE REFERENCE NUMERALS

1 medical information system
101 client terminal
102 modality terminal
NTW, LN network line
200, 200A medical information server
210 medical care subject person information DB
220 imaging test result DB
221 imaging test reading section
230 specimen test result DB
231 specimen test reading section
240 imaging test report DB
241 report registration section
20 search section
23 specimen test search section
24 imaging test report search section
25 search result pairing section
2301 test set DB
2302 report DB

The invention claimed is:

1. A medical information system for communicating a server and a client terminal, the medical information system comprising:

a plurality of databases stored in said server and in which a plurality of kinds of medical data are respectively accumulated;

an input section provided to said client terminal, the input section being operable by a user to input a query that includes a plurality of search items;

a sorting section for sorting said plurality of search items into a plurality of search divisions corresponding to said plurality of databases, respectively, in accordance with a predetermined sorting rule;

a search section for independently searching said plurality of databases by using the search item included in the corresponding search division; and a generation section for combining individual search results extracted respectively from said plurality of databases by said search section, to thereby generate a combined search result, wherein said plurality of databases include:

an imaging test result database in which test images are accumulated; and a finding report storing database in which finding reports corresponding to respective test images and each including a structured-document are accumulated, wherein said search section searches said finding report storing database, for the search item sorted into the search division of a finding report to determine a target finding report in which the search item is described as a structured-element in said structured-document, wherein said generation section includes a test image extraction section for, based on test-image specific information attached to the target finding report obtained as said individual search result, extracting a target test image corresponding to said target finding report from said imaging test result database, and incorporating said target test image into said combined search result, and wherein said structured-document is described in a linguistic relation of different data elements.

2. The medical information system according to claim 1, wherein in said plurality of databases, a plurality of kinds of test diagnosis information are accumulated as said medical data in the databases different from one another, said plurality of kinds of test diagnosis information being records of results of different kinds of clinical tests or diagnostic evaluations on said test results.

3. The medical information system according to claim 2, wherein:

each of said test diagnosis information includes identification information of a medical care subject person or a medical care subject animal serving as a medical care subject individual, and said generation section generates said combined search result by combining, among said test diagnosis information accumulated in said plurality of databases, the information concerning the same medical care subject individual that is identified based on said identification information.

4. The medical information system according to claim 2, wherein:

said plurality of kinds of test diagnosis information have attached thereto information of test identification dates of the corresponding clinical tests, said generation section includes a test identification date score assigning section for assigning a relevancy score indicating a relevancy of different kinds of the test diagnosis information, in such a manner that a higher score is assigned as a difference in the test identification date is smaller, and said generation section combines, across said databases, the test diagnosis information of which said relevancy scores are relatively high, to thereby generate said combined search result.

5. The medical information system according to claim 1, wherein:

said generation section includes an individual score assigning section for assigning an individual score to a content of a data item included in said individual search result obtained from each of said databases, in such a manner that a higher score is assigned as the degree of matching with said search item is higher, and said generation section combines, across said databases, the data items of which said individual scores are relatively high in each of said databases, to thereby generate said combined search result.

6. The medical information system according to claim 5, wherein said individual score is determined based on the ratio of medical data items matching said search items to the medical data in the corresponding database.

7. The medical information system according to claim 1, wherein:

said generation section includes a relevancy score assigning section for assigning, as a relevancy score, a relevancy of said plurality of kinds of individual search results, and said generation section combines, across said databases, the medical data of which said relevancy scores are relatively high, to thereby generate said combined search result.

8. The medical information system according to claim 1, wherein said plurality of databases include a database of at least one of test diagnosis information, nursing care data, electronic medical chart information, and patient information.

9. The medical information system according to claim 8, wherein said plurality of databases include a specimen test result database in which a result of a specimen test is accumulated as said test diagnosis information.

10. The medical information system according to claim 1, wherein:

said generation section includes a report matching degree identification section for identifying a matching degree of each finding report based on how many sentences in said finding report a content matching the search item appears in, and said generation section sets an individual score of each finding report in searching said finding report storing database, based on said matching degree.

11. The medical information system according to claim 1, wherein said structured-document is described in Resource Description Framework.

12. The medical information system according to claim 1, wherein:

a plurality of kinds of medical data based on which a predetermined diagnosis has been previously done are stored across at least two of said plurality of databases, said medical information system further comprises a set information database storing information that identifies a set of said plurality of kinds of medical data, and said generation section refers to said set information database, when combining said plurality of individual search results to obtain said combined search result.

13. A non-transitory computer-readable medium having stored thereon a program that is executable by a computer system comprising a server and a client terminal, a plurality of databases in which different kinds of medical data are respectively accumulated being stored in said server, said program being executable to cause said computer system to function as a medical information system for communicating said server and said client terminal, said medical information system comprising:

an input section provided to said client terminal, the input section being operable by a user to input a query that includes a plurality of search items;

a sorting section for sorting said plurality of search items into a plurality of search divisions corresponding to said plurality of databases, respectively, in accordance with a predetermined sorting rule;

a search section for independently searching said plurality of databases by using the search item included in the corresponding search division; and a generation section for combining individual search results extracted respectively from said plurality of databases by said search section, to thereby generate a combined search result, wherein said plurality of databases include:

an imaging test result database in which test images are accumulated; and a finding report storing database in which finding reports corresponding to respective test images and each including a structured-document are accumulated, wherein said search section searches said finding report storing database, for the search item sorted into the search division of a finding report to determine a target finding report in which the search item is described as a structured-element in said structured-document, wherein said generation section includes a test image extraction section for, based on test-image specific information attached to the target finding report obtained as said individual search result, extracting a target test image corresponding to said target finding report from said imaging test result database, and incorporating said target test image into said combined search result, and wherein said structured-document is described in a linguistic relation of different data elements.

* * * * *